US008840790B2

(12) United States Patent
Wegener et al.

(10) Patent No.: US 8,840,790 B2
(45) Date of Patent: Sep. 23, 2014

(54) SYSTEMS AND METHODS OF CONTROLLING FOULING DURING A FILTRATION PROCEDURE

(75) Inventors: Christopher J. Wegener, Libertyville, IL (US); Marc N. Weasler, West Bend, WI (US); Benjamin E. Kusters, Racine, WI (US); Daniel R. Boggs, Libertyville, IL (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 348 days.

(21) Appl. No.: 13/095,633

(22) Filed: Apr. 27, 2011

(65) Prior Publication Data

US 2012/0273416 A1  Nov. 1, 2012

(51) Int. Cl.
| | | |
|---|---|---|
| B01D 61/32 | (2006.01) | |
| A61M 1/34 | (2006.01) | |
| B01D 65/02 | (2006.01) | |
| B01D 61/22 | (2006.01) | |

(52) U.S. Cl.
CPC ............ B01D 65/02 (2013.01); A61M 1/3496 (2013.01); B01D 61/32 (2013.01); B01D 2321/40 (2013.01); B01D 2311/16 (2013.01); B01D 61/22 (2013.01)
USPC ............ 210/637; 210/645; 210/650; 210/741

(58) Field of Classification Search
USPC ......... 210/636, 637, 645–647, 650–651, 741, 210/90, 137, 138, 321.65; 73/38, 40; 604/4.01–6.16
See application file for complete search history.

(56) References Cited

U.S. PATENT DOCUMENTS

| | | | |
|---|---|---|---|
| 5,034,135 A | | 7/1991 | Fischel |
| 5,069,792 A | | 12/1991 | Prince |
| 5,194,145 A | | 3/1993 | Schoendorfer |
| 5,358,482 A | | 10/1994 | Panzani |
| 5,496,265 A | * | 3/1996 | Langley et al. ............. 604/6.01 |
| 5,587,070 A | | 12/1996 | Pall et al. |
| 5,601,727 A | | 2/1997 | Bormann et al. |
| 5,676,841 A | * | 10/1997 | Brown .......................... 210/739 |
| 5,695,653 A | | 12/1997 | Gsell et al. |
| 5,783,085 A | | 7/1998 | Fischel |
| 5,888,401 A | | 3/1999 | Nguyen |
| 6,113,792 A | | 9/2000 | Benjamin et al. |
| 6,251,284 B1 | | 6/2001 | Bischof |
| 6,463,790 B1 | | 10/2002 | Chun et al. |
| 6,533,747 B1 | | 3/2003 | Polaschegg et al. |
| 6,582,385 B2 | | 6/2003 | Burbank et al. |

(Continued)

OTHER PUBLICATIONS

International Search Report, Written Opinion of the International Searching Authority, and Search History for Int. Appln No. PCT/US12/34055.

*Primary Examiner* — David C Mellon
(74) *Attorney, Agent, or Firm* — Cook Alex Ltd.

(57) ABSTRACT

Systems and methods of controlling fouling during a filtration procedure are described. A plasmapheresis method includes accepting a selection of a plasma flow rate and predicting an estimated procedure end time based at least partially on a plasma collection target volume. The method also includes flowing blood past a membrane and changing a plasma flow rate until the selected plasma flow rate through the membrane is achieved. The method also includes determining an acceptable rate of pressure change with time for respective times to the estimated procedure end time, the acceptable fouling rate limit being associated with a system pressure and adjusting the plasma flow rate based on the determined acceptable rate of pressure change with time.

23 Claims, 15 Drawing Sheets

(56) References Cited

U.S. PATENT DOCUMENTS

| | | |
|---|---|---|
| 6,659,973 B2 | 12/2003 | Gorsuch et al. |
| 6,730,233 B2 | 5/2004 | Pedrazzi |
| 6,890,315 B1 | 5/2005 | Levin et al. |
| 7,074,332 B2 | 7/2006 | Summerton et al. |
| 7,131,956 B1 | 11/2006 | Pirazzoli |
| 7,131,957 B2 | 11/2006 | Müller et al. |
| 7,278,981 B2 | 10/2007 | Ellingboe et al. |
| 7,285,106 B2 | 10/2007 | Collins et al. |
| 7,291,269 B2 | 11/2007 | Chevallet et al. |
| 7,476,210 B2 | 1/2009 | Gorsuch et al. |
| 7,494,590 B2 | 2/2009 | Felding et al. |
| 7,494,591 B2 | 2/2009 | Moriarty et al. |
| 7,531,094 B2 | 5/2009 | McLaughlin et al. |
| 7,674,237 B2 | 3/2010 | O'Mahony et al. |
| 7,744,553 B2 | 6/2010 | Kelly et al. |
| 7,753,869 B2 | 7/2010 | Davidner et al. |
| 7,806,845 B2 | 10/2010 | Arm et al. |
| 7,935,071 B2 | 5/2011 | Levin et al. |
| 7,955,289 B2 | 6/2011 | O'Mahony et al. |
| 7,998,101 B2 | 8/2011 | Ash |
| 8,057,419 B2 | 11/2011 | Ellingboe et al. |
| 8,070,951 B2 | 12/2011 | Benjamin et al. |
| 8,105,260 B2 | 1/2012 | Tonelli et al. |
| 2003/0236482 A1 | 12/2003 | Gorsuch et al. |
| 2005/0260672 A1 | 11/2005 | Couto |
| 2006/0084906 A1 | 4/2006 | Burbank et al. |
| 2007/0215545 A1 | 9/2007 | Bissler |
| 2008/0017576 A1 | 1/2008 | Belfort |
| 2008/0277340 A1 | 11/2008 | Hong |
| 2009/0001018 A1 | 1/2009 | Zha |
| 2010/0012586 A1 | 1/2010 | Angelescu et al. |
| 2010/0137777 A1 | 6/2010 | Kopperschmidt |
| 2010/0280761 A1 | 11/2010 | Balschat et al. |
| 2011/0208106 A1 | 8/2011 | Levin et al. |
| 2012/0010554 A1 | 1/2012 | Vantard et al. |
| 2012/0095381 A1 | 4/2012 | Tonelli et al. |
| 2012/0109037 A1 | 5/2012 | Ellingboe et al. |

\* cited by examiner

SYSTEMS AND METHODS OF CONTROLLING FOULING DURING A FILTRATION PROCEDURE

TECHNICAL FIELD

The present patent pertains to systems and methods of controlling fouling and, more particularly, to systems and methods of controlling fouling during a filtration procedure.

BACKGROUND

During a membrane filtration procedure, membrane fouling may occur that decreases the flow rate through the membrane. Membrane fouling relates to the build up of materials on a membrane surface that decreases fluid flow therethrough. Such membrane fouling may reduce the efficiency of the membrane filtration procedure resulting in longer procedure times.

Figure 1:
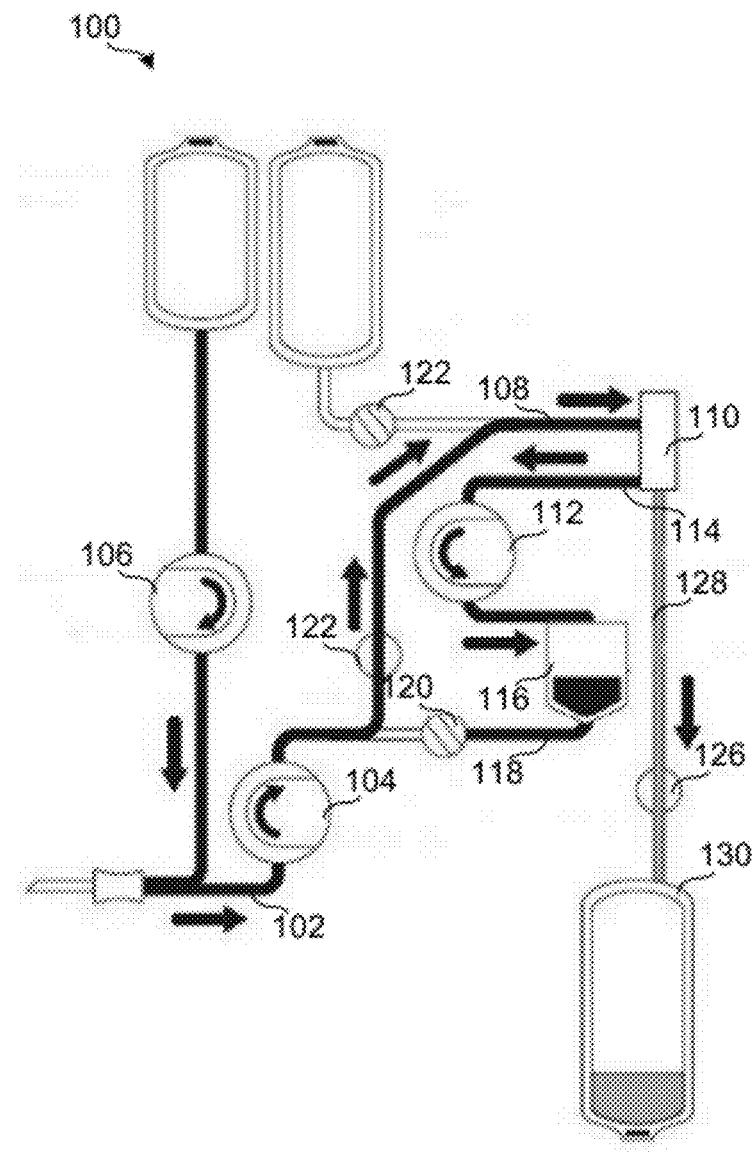
FIG. 1 depicts a system that can implement the examples described herein.

The following detailed description of certain examples, will be better understood when read in conjunction with the appended drawings. For the purpose of illustrating the examples described herein, certain examples are shown in the drawings. It should be understood, however, that the present disclosure is not limited to the arrangements and instrumentality shown in the attached drawings.

DETAILED DESCRIPTION

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification. Any features from any example may be included with, a replacement for, or otherwise combined with other features from other examples.

In some examples, the example systems and methods can be implemented in a plasmapheresis procedure in which a spinning membrane (e.g., a nylon membrane) is used to separate whole blood into plasma and cellular components. In other examples, the example systems and methods can be implemented in a dialysis and/or hemofiltration procedure in which a membrane is used to separate fluid and waste from a patient's blood. Regardless of the type of procedure in which the example systems and methods are implemented, higher sustainable filtrate flow rates may be obtained than observed with known methods. The examples described herein may be used in combination with other methods such as concentrate mixing, backwashing, etc.

The examples described herein relate to systems and methods for controlling fouling to optimize filtrate flow rate during membrane filtration. The examples described herein may be implemented using any suitable system such as the system described in U.S. Pat. No. 5,194,145 and incorporated herein by reference in its entirety. Additionally or alternatively, the examples described herein may be implemented using the system 100 of FIG. 1.

FIG. 1 depicts the example system 100 in a draw cycle configuration during a plasmapheresis procedure. The system 100 includes a donor line 102, an M2 blood pump 104, an M1 anticoagulant pump 106, a processing line 108, a Plasmacell-C® or separation device 110, an M3 red cell pump 112, an in-process line 114, an in-process reservoir 116, a return line 118, clamps 120-126, a plasma line 128 and a plasma collection container 130.

During a draw cycle, as depicted in FIG. 1, blood is continuously drawn into the system 100 from a donor by the M2 blood pump 104 via the donor line 102. The clamp 122 is in the open position and the clamp 120 is in the closed position to direct the donor's whole blood (WB) through the processing line 108 and into a top port of the separation device 110. Within the separation device 110, the donor's WB is separated by a spinning membrane filtration device located therein. Plasma is collected in the plasma collection container 130 via the plasma line 128 and high hematocrit (HCT) blood is pulled by the M3 red cell pump 112 and placed into the in-process reservoir 116. The draw cycle will continue until the in-process reservoir 116 is filled with the HCT blood. Once the in-process reservoir 116 is filled and fluid movement has stopped, the clamp 120 will open and the clamp 122 will close to divert blood flow, allowing for the system 100 to transition to a return cycle.

During the plasmapheresis procedure, membrane fouling may occur in which materials are deposited on a surface of a membrane disposed within the separation device 110. This deposited material increases the resistance of the membrane to fluid flow. Equation 1 represents the rate of fouling, $\dot{F}$, where R represents membrane resistance and t represents time which is a direct measure of the rate of fouling. In some examples, because the units of the fouling rate are pressure per unit volume, such as $mmHg/cm^3$, the fouling rate may be considered an increase in pressure per unit volume of filtrate.

$$\dot{F} = \frac{dR}{dt} \qquad \text{Equation 1}$$

Equation 2 represents the membrane resistance, R, where $P_{TM}$ represents transmembrane pressure and $Q_F$ represents filtrate flow rate.

$$R = \frac{P_{TM}}{Q_F} \qquad \text{Equation 2}$$

Equation 3 depicts Equation 2 being substituted into Equation 1.

$$\dot{F} = \frac{d}{dt}\left(\frac{P_{TM}}{Q_F}\right) \qquad \text{Equation 3}$$

Equation 4 represents Equation 3 in an expanded state.

$$\dot{F} = \frac{1}{Q_F}\frac{dP_{TM}}{dt} - \frac{P_{TM}}{Q_F^2}\frac{dQ_F}{dt} \qquad \text{Equation 4}$$

In a system in which the filtrate flow rate is constant, fouling may be evidenced by an increase in system pressure with time and may be represented by equation 5A.

$$\dot{F} = \frac{1}{Q_F}\frac{dP_{TM}}{dt}. \qquad \text{Equation 5A}$$

In a system in which the pressure is fixed, fouling may be evidenced by a decrease in filtrate flow rate with time and may be represented by equation 5B.

$$\dot{F} = -\frac{P_{TM}}{Q_F^2}\frac{dQ_F}{dt}. \qquad \text{Equation 5B}$$

In a system in which the pressure is forced to increase at a fixed rate, the fouling rate may be represented by Equation 5C below, where $\dot{P} = dP_{TM}/dt$.

$$\dot{F} = \frac{\dot{P}}{Q_F} - \frac{P_{TM}}{Q_F^2}\frac{dQ_F}{dt} \qquad \text{Equation 5C}$$

At a constant transmembrane pressure of approximately 30 mmHg, plasma flow rates may decrease from 40 mL/min to values as low as about 20 mL/min over collection times of approximately 30 minutes. Thus, clinical fouling rates, in accordance with Equation 5B, may be as high as 0.022 mmHg/cm³. Also, in accordance with Equation 5B, filtrate flow rates may be kept constant or made to increase if the pressure ramp, $\dot{P}$, equals or exceeds $\dot{F}Q_F$. However, to ensure that the system 100 is operating below or at the system 100 max pressure, the pressure ramp cannot be arbitrarily high.

Equation 6 represents a rearrangement of Equation 5C in which $dQ_F/dt$ is being solved for.

$$\frac{dQ_F}{dt} = \frac{Q_F}{P_{TM}}(\dot{P} - \dot{F}Q_F) \qquad \text{Equation 6}$$

The filtrate flow rate becomes constant when $\dot{P} - \dot{F}Q_F = 0$.

Figure 1A:
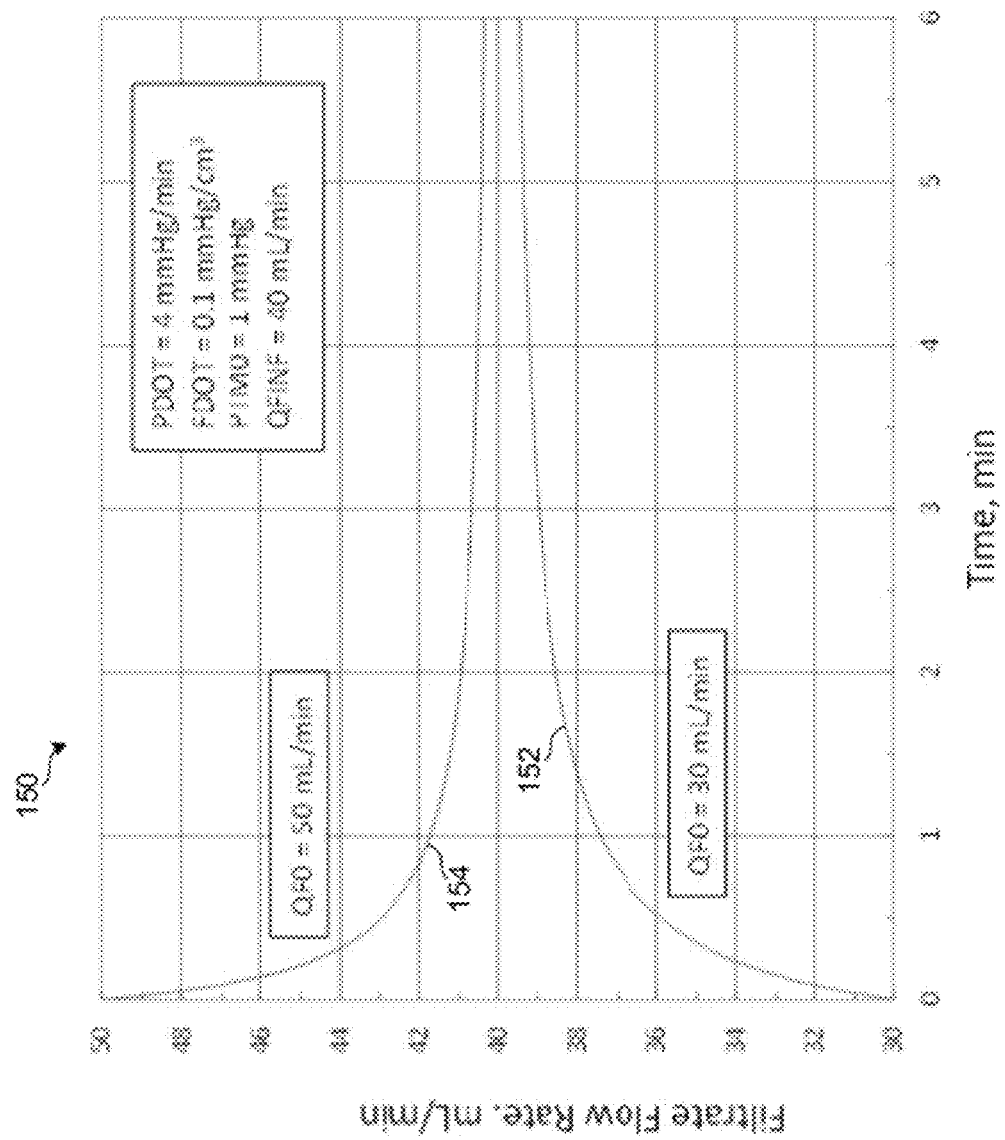
FIG. 1A illustrates an example transient response in filtrate flow rate.

FIG. 1A depicts a solution 150 to Equation 6 when a fouling rate is constant with initial filtrate flow rates above and below an asymptotic value (e.g., 40 mL/min). More specifically, FIG. 1A, illustrates a transient response in filtrate flow rate upon imposition of a constant pressure ramp ($\dot{P}$) of 4 mmHg/min and a constant fouling rate ($\dot{F}$) of 0.1 mmHg/cm³. For a curve 152 below the asymptotic value, the filtrate flow rate at time=0 (QF0) is 30 mL/min and for a curve 154 above the asymptotic value, the filtrate flow rate at time=0 (QF0) is 50 mL/min. The transmembrane pressure at time=0 (PTMO) is 1 mmHg and the filtrate flow rate at time=infinity (QFINF) is 40 mL/min.

Figure 2:
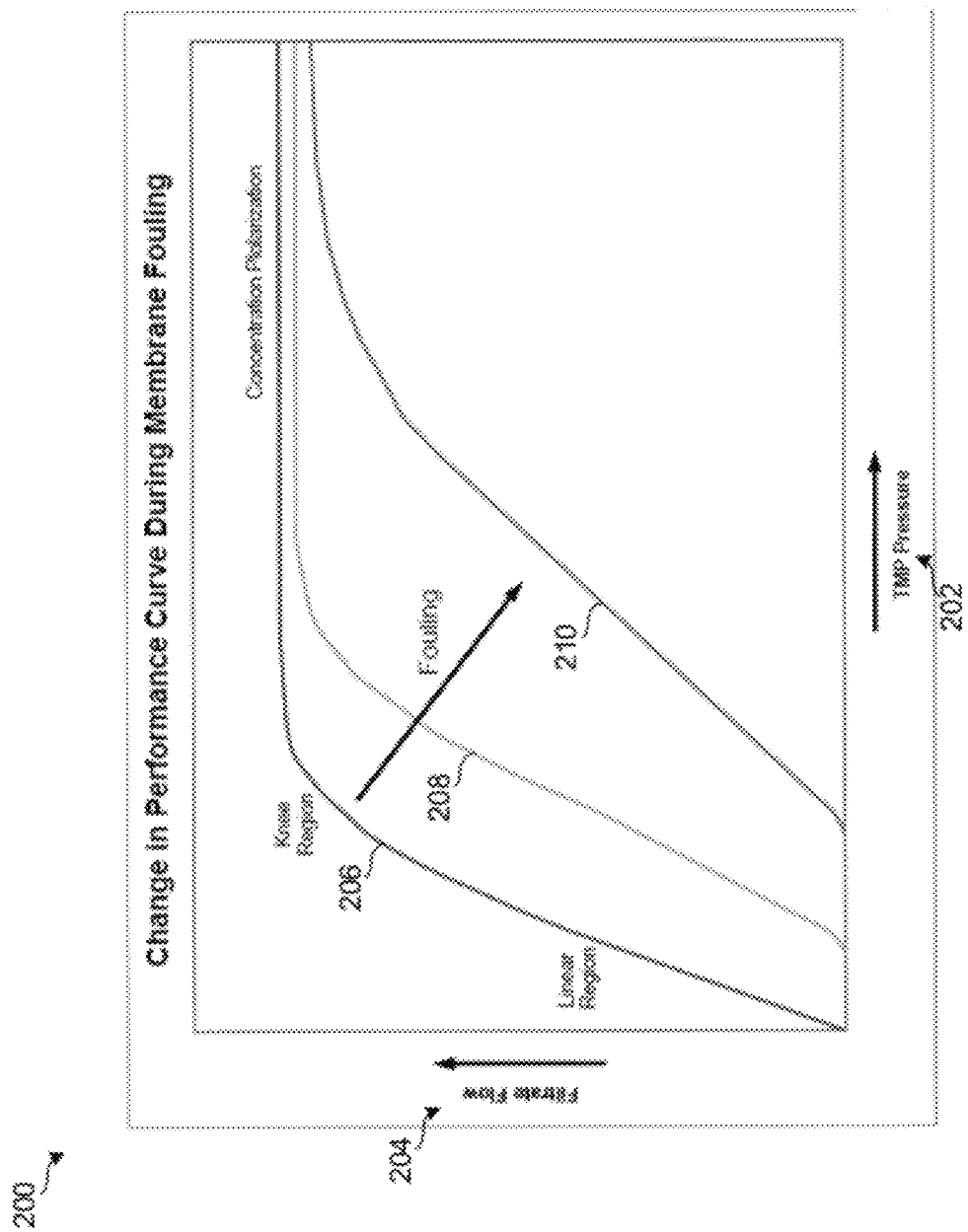
FIG. 2 depicts performance curves during membrane fouling.

FIG. 2 is a graph 200 depicting a change in performance during membrane fouling. The x-axis 202 relates to TMP pressure and the y-axis 204 relates to filtrate flow. Transmembrane pressure (TMP) relates to a pressure that drives plasma flow across a membrane. Curve 206 represents an initial performance curve of a membrane filtration device and curves 208 and 210 depict performance curves as fouling occurs, respectively. Referring to curve 206, at low TMP pressures, an amount of filtrate flow is linearly proportional to the amount of TMP pressure generated. However, as the TMP pressure is increased, as shown in a "knee" region of the curve 206, a relationship between the TMP pressure and the filtrate flow rate changes such that an increase in the TMP pressure does not cause a proportional increase in the filtrate flow rate. When a concentration polarization limit is met, increases in the TMP pressure no longer increases the filtrate flow rate through the membrane because mixing present in the system is not adequate to clear away the particulate matter that builds up on the membrane surface.

During a plasmapheresis procedure, fouling may occur that irreversibly clogs pores of the membrane creating increased membrane resistance and requiring additional pressure to generate the same filtrate flow rate. As depicted by the curves 206, 208 and 210, as fouling occurs, the linear region, the "knee" region and the concentration polarization limit remain intact; however, the relationship(s) between these three regions change such that the slope of the linear region lessens and the TMP pressure to generate the same filtrate flow is shifted upward.

Figure 3:
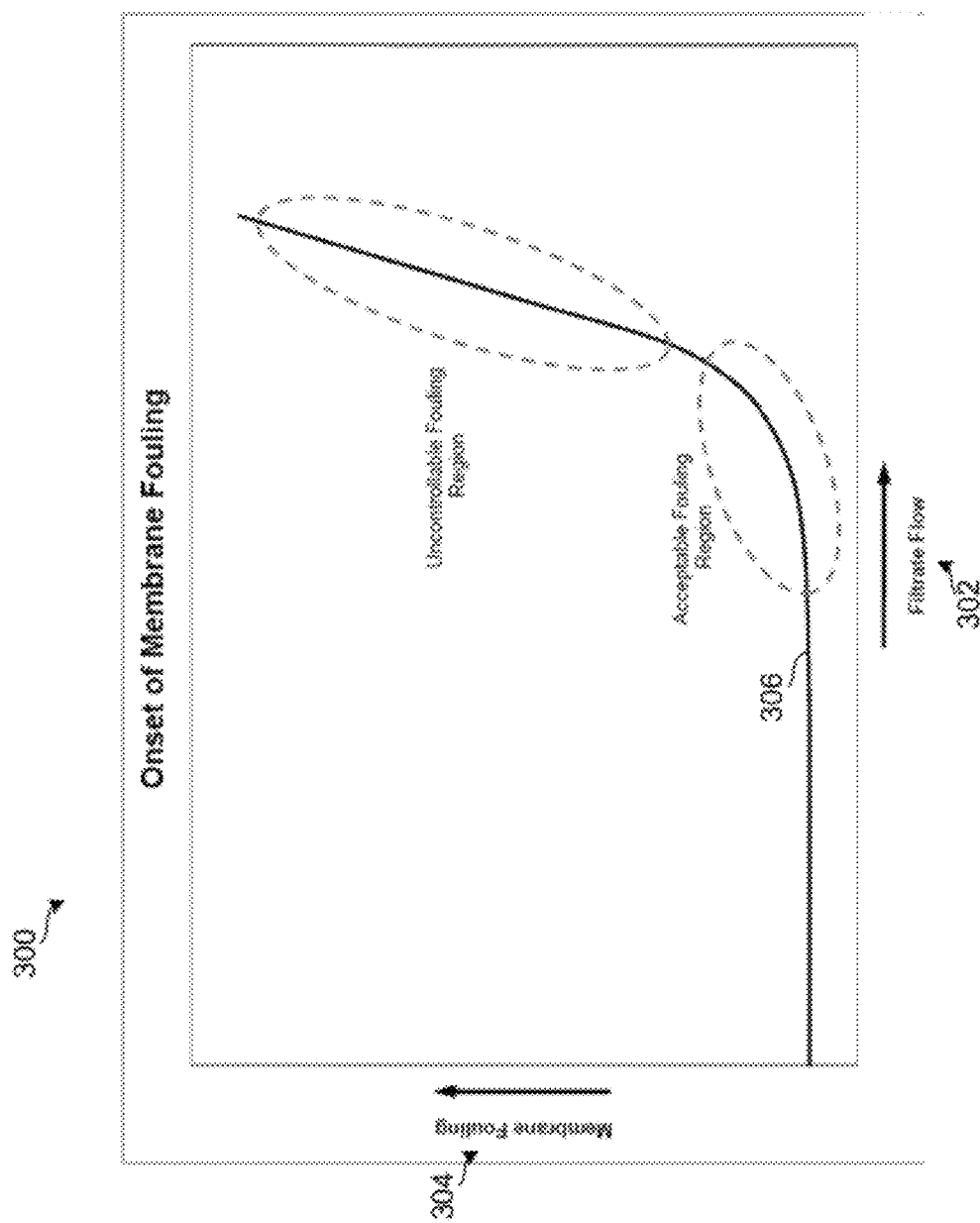
FIG. 3 depicts a curve representing the onset of membrane fouling.

FIG. 3 depicts a graph 300 of membrane fouling. The x-axis 302 relates to filtrate flow and the y-axis 304 relates to membrane fouling. As represented by the curve 306, at relatively low filtrate flow rates, little to no fouling may be observed and, thus, the TMP pressure may remain constant. However, as the filtrate flow rates are increased, the risk of causing membrane fouling also increases. At relatively high filtrate flow rates, membrane fouling may occur at uncontrollable rates causing the TMP pressure to increase dramatically and/or exponentially.

In some applications, such as those using the examples described herein, some pressure increases may be tolerated. For example, in filtration systems in which the pressure increases during a duration of the procedure, an acceptable fouling rate may be selected that enables the system to operate efficiently and within the acceptable fouling rate region.

Figure 4:
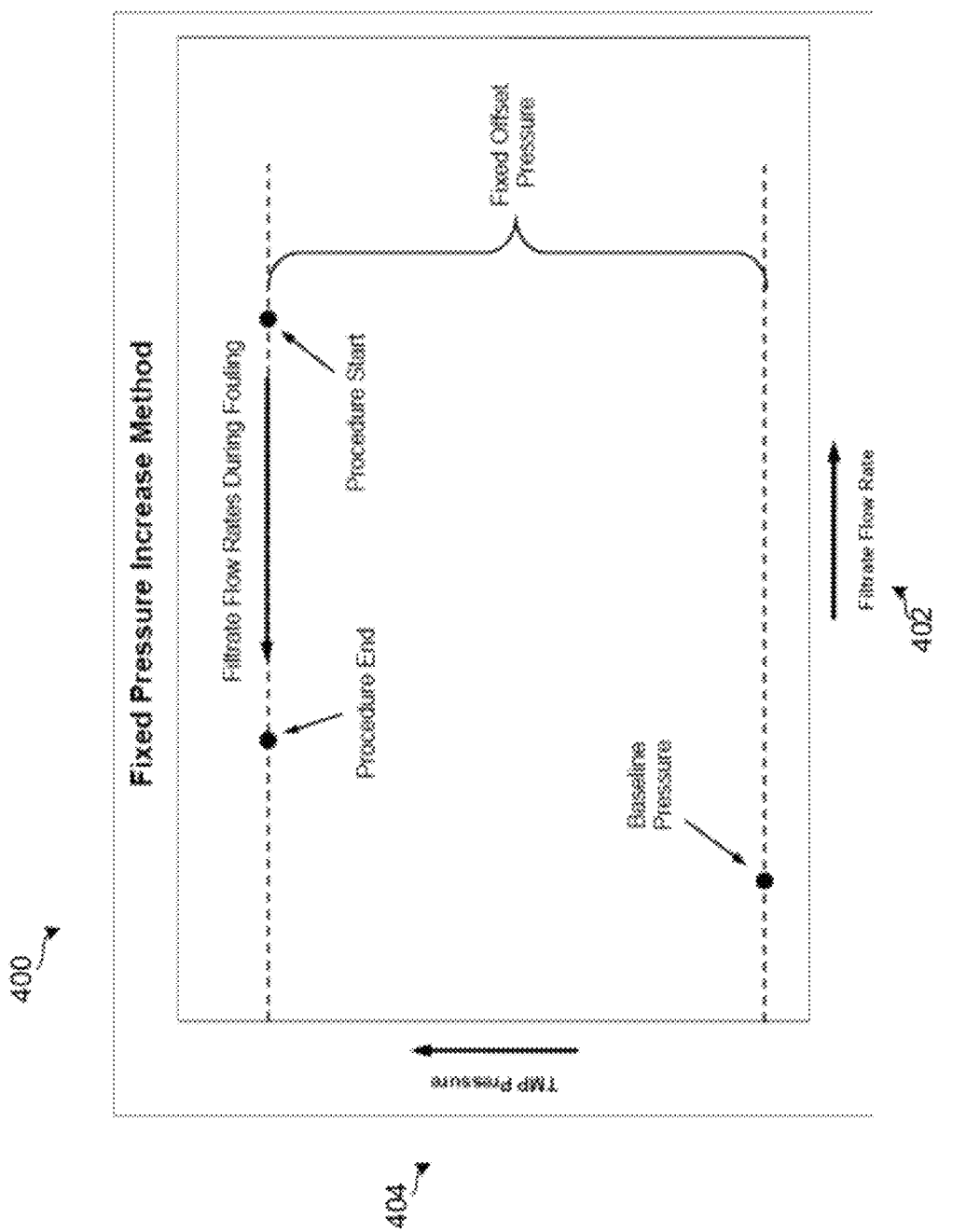
FIG. 4 depicts a graph representing results using a known pressure increase method.

FIG. 4 depicts a graph 400 relating to a fixed pressure increase method used in some known plasmapheresis procedures. An x-axis 402 relates to filtrate flow rate and a y-axis 404 relates to TMP pressure. In this method, a baseline pressure is measured and a fixed offset pressure is applied to the system to generate filtrate flow through the membrane. Depending on the preset pressure selected, membrane fouling may be generated and may not be adjusted for during the procedure. If membrane fouling is generated, the filtrate flow rate may decrease proportionally to the amount of fouling present in the system resulting in significantly lower filtrate flow rates at the end of the procedure than at the beginning of the procedure. Because the fixed pressure increase method assumes that TMP pressure and filtrate flow rates are linearly related, which is untrue at higher TMP pressures, this method may select smaller off-set pressures to enable the system to operate in the linear region of the performance curve of FIG. 2 and to avoid fouling. If a larger off-set pressure is selected, the system may initially generate higher filtrate flow rates; however, due to the fouling generated, overtime, the filtrate flow rate decreases because the target pressure method inaccurately assumes TMP pressure and filtrate flow rates are always linearly related.

Figure 5:
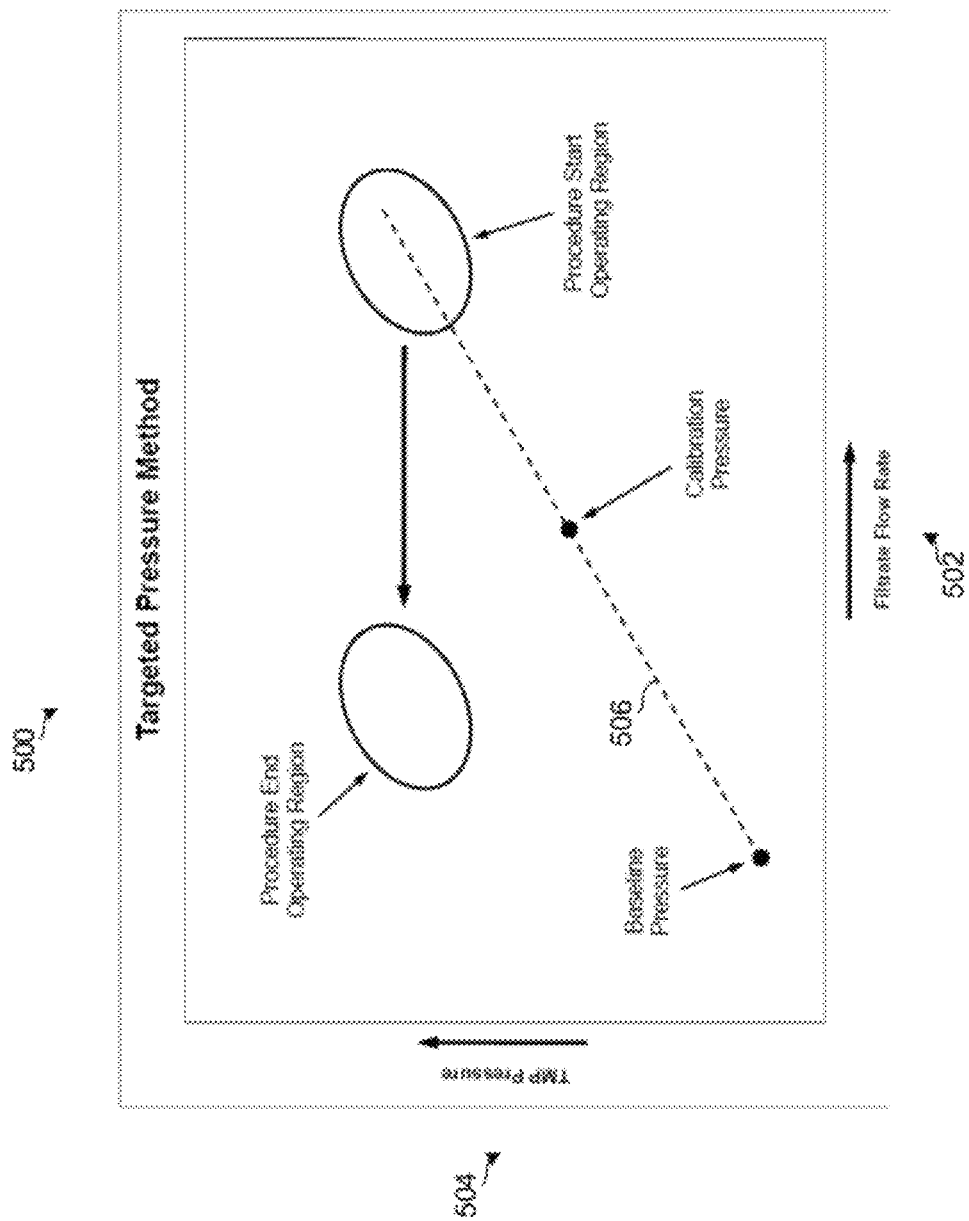
FIG. 5 depicts a graph representing results using a known target pressure method.

FIG. 5 depicts a graph 500 relating to a target pressure method used in some known plasmapheresis procedures. The x-axis 502 relates to filtrate flow rate and the y-axis 504 relates to TMP pressure. The target pressure method requires a baseline pressure measurement where no filtrate flow rate is demanded and calibration pressure measurements where conservative filtrate flow rates are demanded. Using the baseline pressure measurement and the calibration pressure measurements, a line 506 may be drawn between and beyond the two points that represents the TMP pressure needed to generate a particular flow rate. However, as with the fixed pressure increase method, at higher TMP pressures, fouling occurs that decreases the filtrate flow rate as the procedure progresses because the target pressure method also assumes that the TMP pressure and the filtrate flow rates are linearly related.

Figure 6:
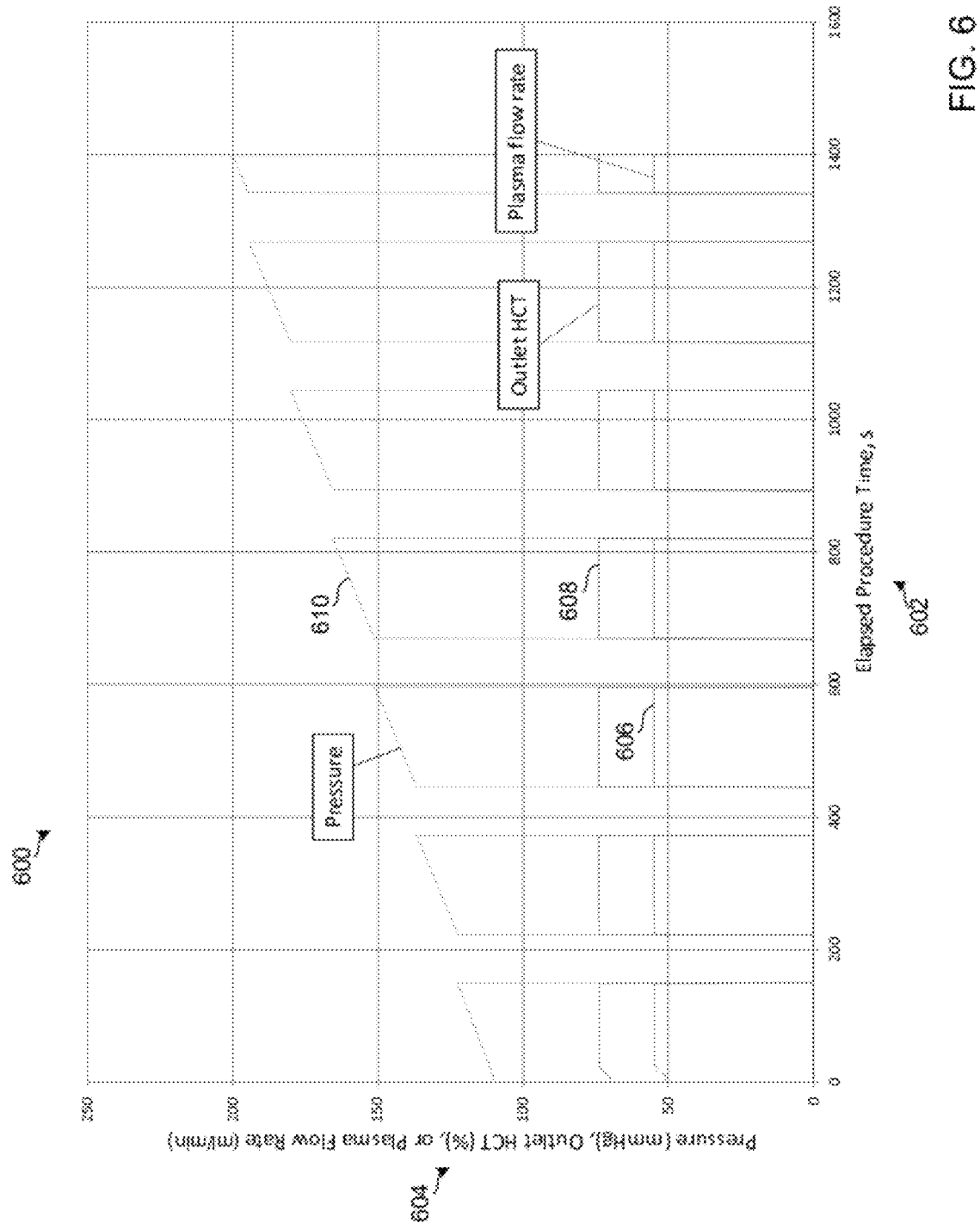
FIGS. 6 and 6A depict example simulations using the examples described herein.

FIG. 6 depicts an example simulation 600 using the examples described herein for an initial demanded outlet hematocrits ($H_o0$) of 70%. The results indicate that, using the examples described herein, a plasmapheresis procedure end time may be approximately 23.8 minutes. At least some additional simulation input parameters may include an inlet hematocrit ($H_I$) of 42%; a reservoir volume ($V_R$) of 180 mL; an inlet blood flow rate ($Q_I$) of 127 mL/min; a return blood flow rate ($Q_R$) of 150 mL/min; a transition time ($T_T$) of 0 sec.; a volume of plasma to be collected ($V_P$) of 880 mL; a maximum pressure ($P_{MAX}$) of 200 mmHg; an initial pressure ($P_I$) of 105 mmHg; an update period ($D_T$) of 1 sec; and a pressure observation time ($T_S$) of 10 sec.

Referring to the simulation 600 results, the x-axis 602 relates to an elapsed procedure time and the y-axis 604 relates to pressure, outlet HCT or plasma flow rate. A first plurality of line segments 606 relates to plasma flow rate, a second plurality of line segments 608 relates to outlet HCT and a third plurality of line segments 610 relates to pressure. Each of the line segments is associated with a different draw cycle during a plasmapheresis procedure and each of the spaces between the line segments is associated with a different return cycle during the plasmapheresis procedure.

At the beginning of a draw cycle, a target value of the plasma flow rate, $Q_F$, is calculated from inputs. The procedure may begin by demanding that plasma flow rate and noting the pressure, P, for a certain time period, $T_S$. At the end of the time period, $T_S$, the collection time remaining during the plasmapheresis procedure, $T_R$, may be calculated by dividing the plasma volume remaining to be collected by the plasma flow rate ($T_R = P_V/Q_F$), for example. To obtain a target pressure ramp, $\dot{P}$, the collection time remaining may be divided into the difference between the last measured pressure value and the maximum system pressure value, $P_{MAX}$. The target pressure ramp (e.g., pressure increase with time) may be imposed on the system for the remainder of a draw cycle that ends when a blood volume in a reservoir, $V_R$, exceeds the maximum reservoir volume value, $V_{RT}$. At the end of each draw cycle, the reservoir is drained at a rate of $Q_R$ and then the process begins again. The process continues until the plasma collected, $V_P$, is equal to the plasma target amount, $V_{PT}$. Once the plasma target amount has been collected, the reservoir is drained a final time.

In some examples, input for the fouling rate may be obtained from experiments, such as from experiments conducted using the Plasmacell-C® device of Fenwal® Inc. The experimentally derived fouling rate, $\dot{F}$, for Plasmacell-C® device may be represented by Equation 7, below, where $H_o$ represents outlet hematocrit and $Q_F$ represents plasma flow rate.

$$\dot{F} = \frac{200}{(80 - H_O)^2 Q_F} \quad \text{Equation 7}$$

The plasma flow rate, $Q_F$, may be determined using Equation 8, below, using the fourth order Runge-Kutta method, where $P_{TM}$ represents transmembrane pressure.

$$\frac{dQ_F}{dt} = \frac{Q_F}{P_{TM}}(\dot{P} - \dot{F}Q_F) \quad \text{Equation 8}$$

In some examples, the collection time remaining, $T_R$, may be calculated assuming a zero transition time using Equation 9, below, where $V_{PR}$ represents the volume of plasma remaining to be collected.

$$T_R = \frac{V_{PR}}{Q_F} \quad \text{Equation 9}$$

Figure 6A:
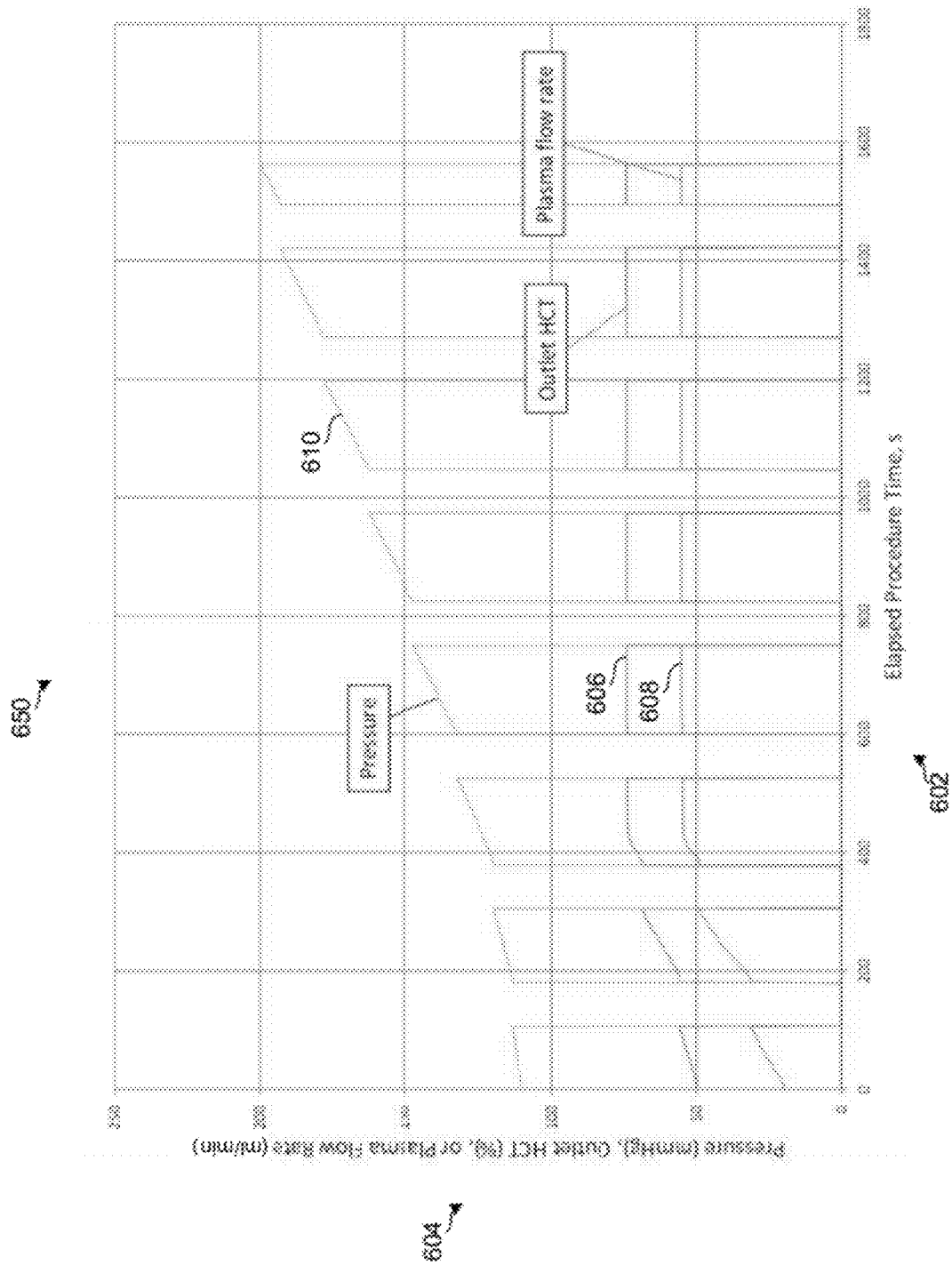

FIG. 6A depicts an example simulation 650 using the examples described herein for an initial demanded outlet hemocrits of 50%. The results indicate that, using the examples described herein, a plasmapheresis procedure end time may be approximately 26.2 minutes. At least some additional simulation input parameters may include an inlet hematocrit ($H_I$) of 42%; a reservoir volume ($V_R$) of 180 mL; an inlet blood flow rate ($Q_I$) of 127 mL/min; a return blood flow rate ($Q_R$) of 150 mL/min; a transition time ($T_T$) of 0 sec.; a volume of plasma to be collected ($V_P$) of 880 mL; a maximum pressure ($P_{MAX}$) of 200 mmHg; an initial pressure ($P_I$) of 105 mmHg; an update period ($D_T$) of 1 sec; and a pressure observation time ($S_T$) of 10 sec. Referring to the simulation results 650, reference numbers of FIG. 6 are used to represent similar segments of the simulation 650.

Figure 7:
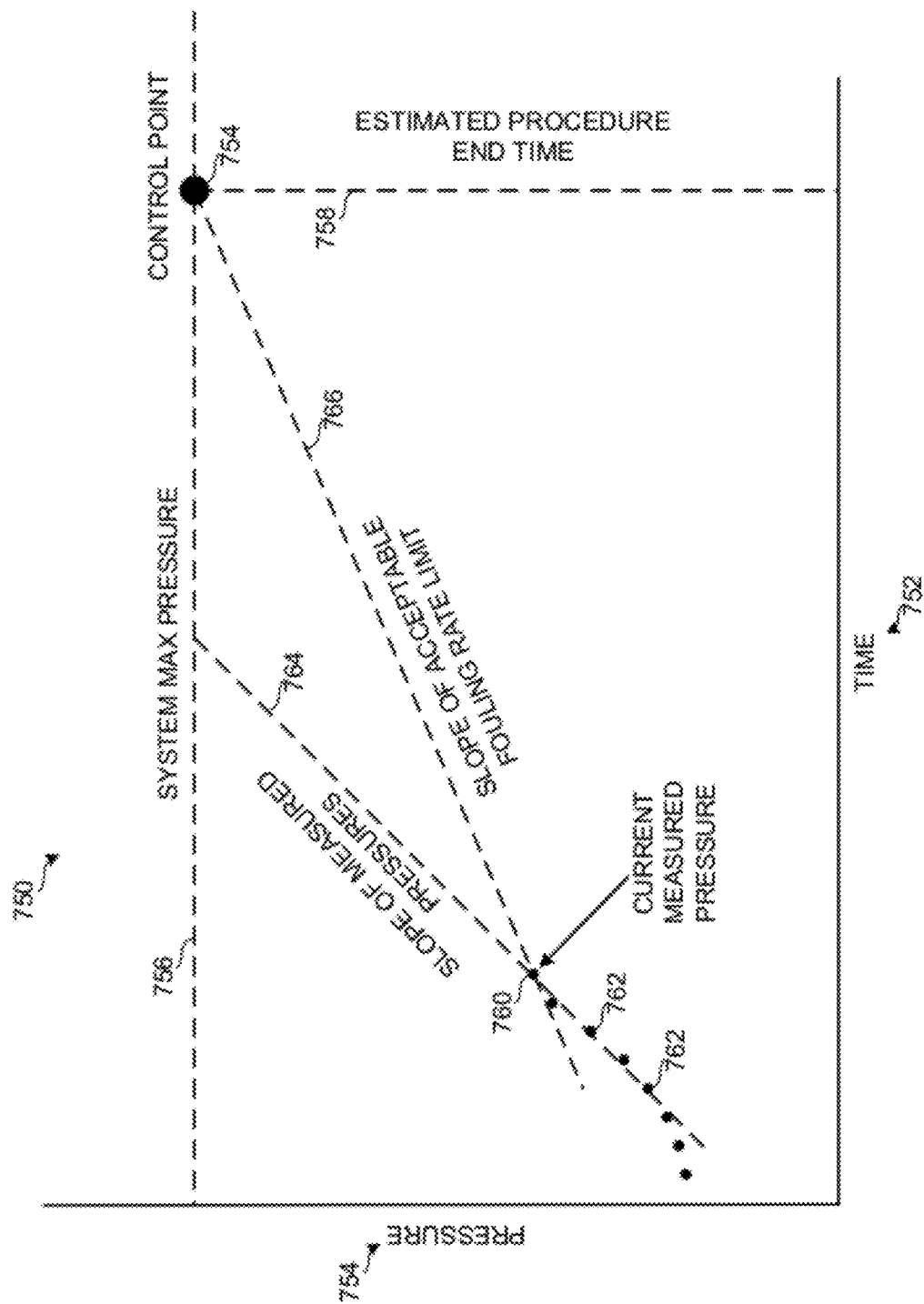
FIG. 7 depict graphs representing results using examples described herein.

FIG. 7 represents results 750 associated with the examples described herein. The x-axis 752 represents time and the y-axis 754 represents pressure. Prior to and/or while a plasmapheresis procedure is taking place, a control point 754 may be calculated that is related to a system max pressure 756 and an estimated procedure end time 758. The control point 754 may be the point at which the plasma collection target is reached and the maximum system pressure has been simultaneously reached, thereby maximizing system efficiency. The control point 754 may be recalculated during the procedure such as, at periodic instances and/or when a pressure measurement is taken. Pressure measurements may be taken at periodic intervals and such measurements may be recorded and/or plotted. As illustrated in FIG. 7, a current pressure measurement may be represented by reference number 760 and previous pressure measurements may be represented by reference number 762.

In some examples, at every instance that the pressure of the system is measured, the system may determine a slope of the measured pressures 764 and a slope of the acceptable fouling rate limit 766 (e.g., the slope between the current measured pressure 760 and the control point 754). As discussed above, the control point 754 may be recalculated as the procedure progresses. Based on the comparison between the slopes, the system may adjust the pressure such that as additional pressure measurements are taken, the slope of all or some of the measured pressures (e.g., the measured pressures during a draw cycle) is similar to the slope between the last pressure measured (i.e., the new current pressure measurement) and the control point. As illustrated in FIG. 7, in this example, the slope of the measured pressures 764 is greater than the slope of the acceptable fouling rate limit 766. Thus, the system may adjust the pressure such that as the procedure progresses, the slope of the measured pressures is reduced and more similar to the slope of the newly determined acceptable fouling rate limit (i.e., the slope between the current measured pressure and a control point).

Additionally or alternatively, if the observed fouling rate (e.g., the rate of change of the inlet pressure with time) exceeds the acceptable fouling rate calculated using the examples described herein, the system may respond by decreasing the demanded plasma flow rate until the observed fouling rate is at the acceptable fouling rate limit. Alternatively, during a plasmapheresis procedure, if the observed fouling rate (e.g., the rate of change of the inlet pressure with time) is less than the acceptable fouling rate calculated using the examples described herein (e.g., little to no membrane fouling being observed), the system may respond by increasing the demanded plasma flow rate until the observed fouling rate is at the acceptable fouling rate limit.

Figure 8:
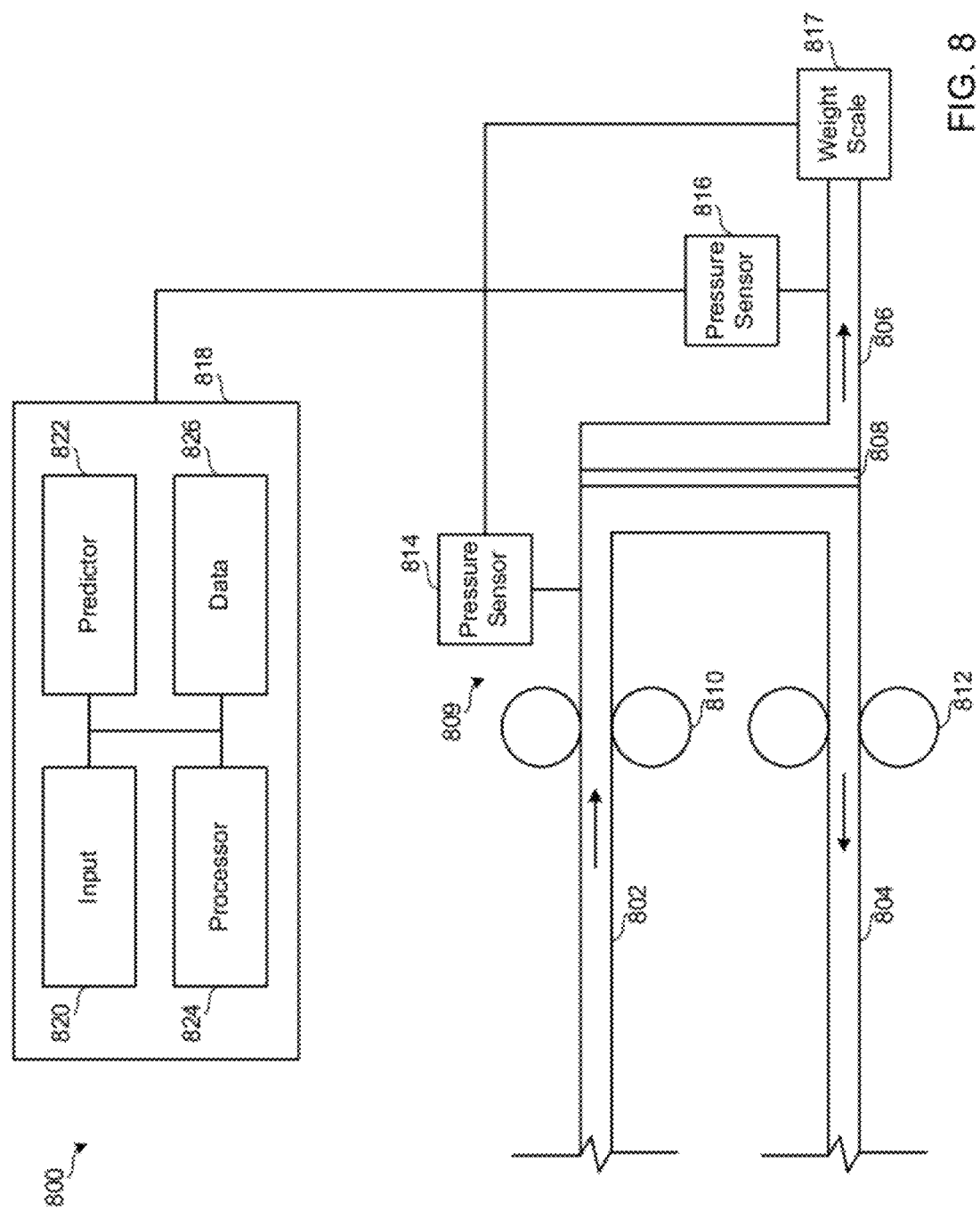
FIG. 8 depicts an example system that can be used to implement the examples described herein.

FIG. 8 depicts a schematic representation of an example system 800 that can be used to implement the examples described herein. The system 800 includes a plurality of flow lines including a bulk flow line 802, a concentrate flow line 804 and a filtrate flow line 806. The filtrate flow line 806 may be separated by the flow lines 802 and 804 by a membrane 808 that is part of a separation device 809. In some examples, blood from a donor may flow through the bulk flow line 802 toward the membrane 808, cellular components of the blood too large to pass through the membrane 808 may flow through the concentrate flow line 804 and plasma and other small cellular components that pass through the membrane 808 may flow through the filtrate flow line 806. The cellular components too large to pass through the membrane 808 may be returned to the donor and the plasma and small cellular components may be collected. The system 800 additionally includes a first or feed pump 810 and a second or concentrate pump 812. One or both of the pumps 810 and/or 812 may be implemented as peristaltic pumps.

The system 800 may include a first pressure sensor 814 adjacent the bulk flow line 802 and/or a second pressure sensor 816 adjacent the filtrate flow line 806 both of which may be used to determine TMP pressure during a plasmapheresis procedure or any other filtration procedure if the filtrate flow line 806 is not open to atmospheric pressure. However, if the filtrate flow line 806 is open to atmospheric pressure, the system 800 may not include the second pressure sensor 816 as, in such instances, TMP pressure may be determined using just the first pressure sensor 814. To monitor the flow rate through the filtrate flow line 806 and/or to measure the amount of filtrate collected, the system 800 may include a weight scale 817.

The system 800 additionally includes a fouling rate control apparatus 818. The apparatus 818 may include an input 820, a predictor 822, a processor 824 and a data store and/or source 826. While an example manner of implementing the system 800 has been illustrated in FIG. 8, one or more of the elements, processes and/or devices illustrated in FIG. 8 may be combined, divided, re-arranged, omitted, eliminated and/or implemented in other ways. In some examples, the processor 824 may be integrated into the input 820, the predictor 822 and/or the data source 826.

The input 820, the predictor 822, the processor 824 and/or the data source 826 and, more generally, the example apparatus 818 may be implemented by hardware, software, firmware and/or a combination of hardware, software and/or firmware. Thus, the input 820, the predictor 822, the processor 824 and/or the data source 826 and, more generally, the example apparatus 818 can be implemented by one or more circuit(s), programmable processor(s), application specific integrated circuit(s) (ASIC(s)), programmable logic device(s) (PLD(s)) and/or field programmable logic device(s) (FPLD(s)), etc. When any of the appended claims are read to cover a purely software and/or firmware implementation, at least one of the input 820, the predictor 822, the processor 824 and/or the data source 826 and, more generally, the example apparatus 818 are hereby expressly defined to include a tangible medium such as a memory, DVD, CD, Blu-ray, etc., storing the software and/or firmware. Further still, the example apparatus 818 of FIG. 8 may include one or more elements, processes and/or devices in addition to, or instead of, those illustrated in FIG. 8, and/or may include more than one of any or all of the illustrated elements, processes and devices.

During and/or prior to a plasmapheresis procedure, the predictor 822 may estimate a procedure end time to separate at least some of the plasma from the blood. In some examples, the estimated procedure end time may be determined using the equations described above. The processor 824 may identify a control point based on the estimated procedure end time, the max and/or end time pressure of the system 800 and/or a plasma collection target, etc., for example.

During a plasmapheresis procedure, blood from a donor may be pumped into the separation device 809 through the bulk flow line 802 using the first pump 810. In some examples, the blood may flow through the bulk flow line 802 at a rate of approximately 100 mL/min. The blood may be pumped out of the separation device 809 through the concentrate flow line 804 using the second pump 812. In some examples, the blood may flow through the concentrate flow line 804 at a rate of approximately 70 mL/min. To overcome resistance of the membrane 808 and cause plasma to pass therethrough, the first pump 810 may pump the blood at a first rate and the second pump 812 may pump the blood at a second rate to generate a TMP pressure. The TMP pressure may be associated with the plasma flow rate through the membrane 808.

The difference between the first pump 810 rate and the second pump 812 rate may be based on a selected filtrate flow rate and/or a plasma flow rate received by the input 820. In some examples, the selected plasma flow rate may be approximately 30 mL/min. As the plasma begins to flow through the membrane 808, the difference between the pump rates may change causing the TMP pressure to increase until the selected plasma flow rate through the membrane 808 is achieved. The weight scale 817 may determine the plasma flow rate through the filtrate flow line 806 and/or the membrane 808 by weighing the plasma collected.

Once the selected plasma flow rate has been achieved, the processor 824 may extrapolate a line that represents an acceptable fouling rate limit from the time and pressure at which the selected plasma flow rate is achieved to the control point. A slope of the line may represent the acceptable fouling rate limit.

As the plasma flows through the membrane 808 and/or the plasmapheresis procedure proceeds, the pressure sensor(s) 814 and/or 816 may monitor a pressure of the fluid (e.g., bulk fluid, filtrate fluid) adjacent thereto. The TMP pressure may steadily increase during the plasmapheresis procedure because of the occurrence of membrane 808 fouling as plasma and other cellular components flow through the membrane 808. The steady increase in TMP pressure may occur even if the difference between the rate of the first pump 810 and the second pump 812 remains constant.

The acceptable increase in TMP pressure during the plasmapheresis procedure may be represented by the slope of the acceptable fouling rate limit. The acceptable fouling rate limit may be recalculated at each pressure measurement and/or during each draw cycle, for example. If a steady increase in the TMP pressure at respective procedure times is above the acceptable fouling rate limit (e.g., there is a difference between the slope of the measured pressures and the slope between the current pressure and the control point), the processor 824 may cause the second pump 812 to increase its rate causing the plasma flow rate through the membrane 808 to decrease. The decrease in the plasma flow rate through the membrane 808 may also decrease the TMP pressure and decrease the fouling rate. If a steady increase in the TMP pressure at respective procedure times is below the acceptable fouling rate limit (e.g., there is a difference between the slope of the measured pressures and the slope between the current pressure and the control point), the processor 824 may cause the second pump 812 to decrease its rate causing the plasma flow rate through the membrane 808 to increase. The decrease in the plasma flow rate through the membrane 808 may also increase the TMP pressure and increase the fouling rate. Once the procedure end time has been achieved and/or the plasma collection target has been reached, the plasmapheresis procedure may end.

The processor 824 may drive the input 820 to enable data to be displayed and/or entered. The processor 824 may drive the predictor 822 to predict an estimated procedure end time. The apparatus 818 may include one or more internal memories and/or data stores including the data source 826. Data storage can include any variety of internal and/or external memory, disk, remote storage communicating with the apparatus 818 and/or the system 800.

FIGS. 9-12 depict example flow diagrams representative of processes that may be implemented using, for example, computer readable instructions that may be used to control fouling to optimize filtrate flow rate during a fluid filtering process using one or more of a fouling rate control apparatus, a data store, a processor and/or a system. The example processes of FIGS. 9-12 may be performed using a processor, a controller and/or any other suitable processing device. For example, the example processes of FIGS. 9-12 may be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. Additionally or alternatively, the example processes of FIGS. 9-12 may be implemented using coded instructions (e.g., computer readable instructions) stored on a non-transitory computer readable medium such as a flash memory, a read-only memory (ROM), a random-access memory (RAM), a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, some or all of the example processes of FIGS. 9-12 may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIGS. 9-12 may be implemented manually or as any combination(s) of any of the foregoing techniques, for example, any combination of firmware, software, discrete logic and/or hardware. Further, although the example processes of FIGS. 9-12 are described with reference to the flow diagrams of FIGS. 9-12, other methods of implementing the processes of FIGS. 9-12 may be employed. For example, the order of execution of the blocks may be changed, and/or some of the blocks described may be changed, eliminated, sub-divided, or combined. Additionally, any or all of the example processes of FIGS. 9-12 may be performed sequentially and/or in parallel by, for example, separate processing threads, processors, devices, discrete logic, circuits, etc.

Figure 9:
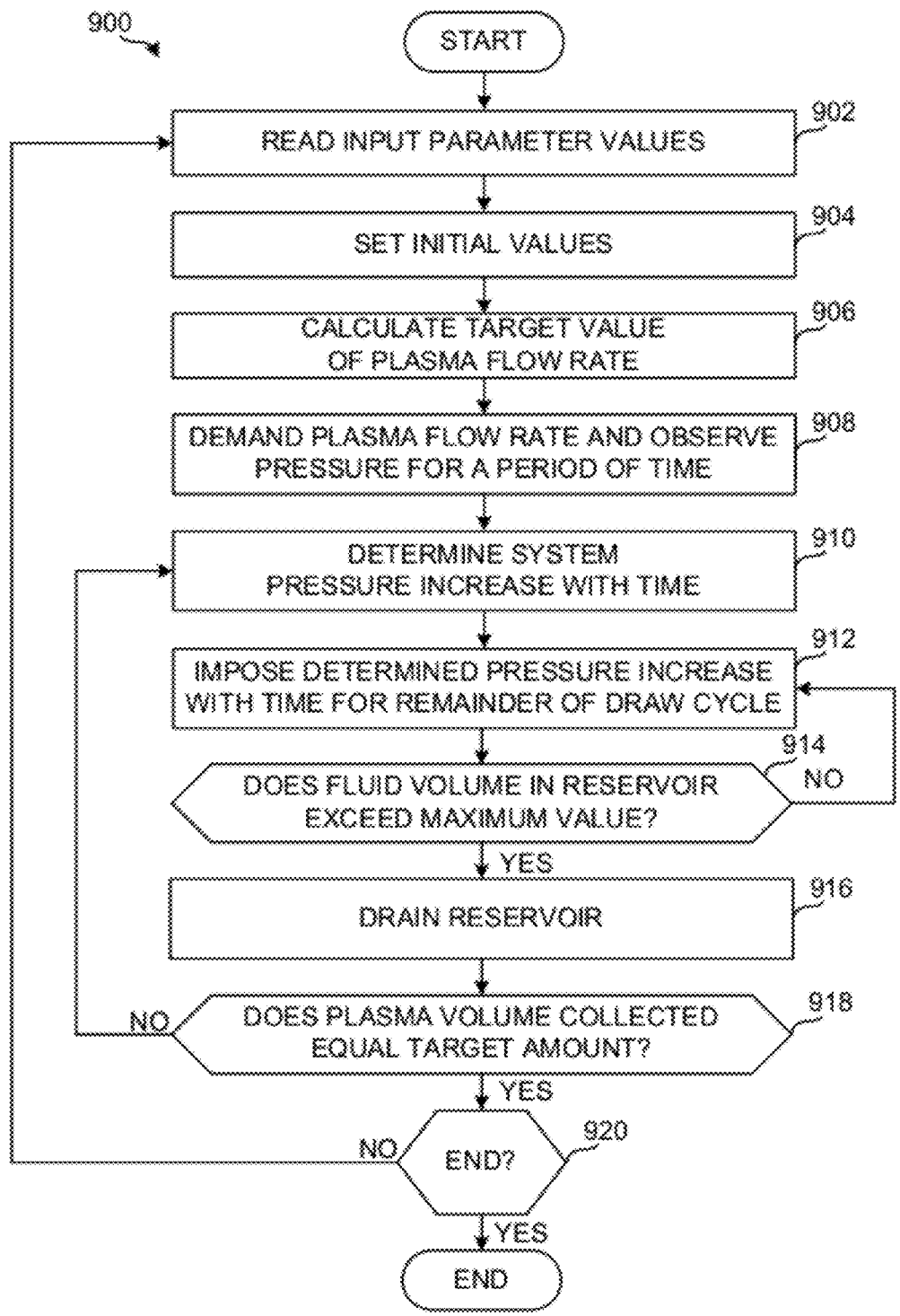
FIGS. 9-12 are flow diagrams of example methods that can be used to implement the examples described herein.

FIG. 9 relates to an example method 900 of controlling fouling to optimize filtrate flow rate during a plasmapheresis procedure. At block 902, the method 900 may read input parameter values. The parameter values may have been entered by an operator, retrieved from a data store and/or based on measurements taken. The parameter values may include inlet hematocrit, initial demanded outlet hematocrit, the blood reservoir maximum value, inlet blood flow rate, return blood flow rate, transition time, plasma target amount, system maximum pressure, the system initial pressure, the update period and/or the time period for pressure behavior observation.

At block 904, the method 900 sets at least some initial values. For example, the plasma volume collected may be set to zero, the procedure time may be set to zero, the outlet hematocrit may be set to the initial value, the pressure may be set to the initial value (e.g., pressure initial plus the initial transmembrane pressure), the cycle is set to 1, the plasma remaining to be collected is set to the plasma target amount and/or the fluid volume in the reservoir is set to 0.

At block 906, the method 900 calculates a target value of the plasma flow rate. The plasma flow rate may be calculated from the outlet hematocrit and/or by equation 10 below, where $Q_P$ represents the plasma flow rate, $Q_I$ represents the inlet blood flow rate, HI represents the inlet hematocrit and $H_o$ represents the outlet hematocrit.

$$Q_P = Q_I\left(1 - \frac{H_I}{H_O}\right) \quad \text{Equation 10}$$

The method 900 may also determine the estimated procedure time remaining and/or the estimated collection time remaining. The estimated procedure time remaining may be determined using equation 11 below, where $$F = \frac{(Q_I - Q_P)}{Q_R},$$

$V_p$ represents the volume of plasma to be collected and $Q_P$ represents the plasma flow rate.

$$\text{Procedure Time Remaining} = \frac{V_P(1+F)}{Q_P} \quad \text{Equation 11}$$

The estimated collection time remaining may be determined using equation 12 below, where $V_{PT}$ represents the target volume of plasma to be collected, $V_P$ represents the volume of plasma already collected and $Q_P$ represents the current plasma flow rate.

$$\text{Collection Time Remaining } (T_R) = \frac{V_{PT} - V_P}{Q_P} \quad \text{Equation 12}$$

At block 908, the method 900 demands the plasma flow rate and observes and/or notes the system pressure for a period of time, $T_S$. During the observation period, the outlet flow rate may be determined using equation 13 below. Additionally or alternatively, during the observation period, the slope of the measured pressures may be determined.

$$Q_O = Q_r - Q_P \quad \text{Equation 13:}$$

The fouling rate may be determined using equation 14 below.

$$\text{Fouling Rate } (\dot{F}) = \frac{200}{((80 - H_O)^2 Q_P)} \quad \text{Equation 14}$$

The pressure increase of the system with time may be determined using equation 15 below. Alternatively and as discussed above, the pressure increase of the system with time may be measured.

$$\text{Pressure Increase with Time} \left(\frac{dP}{dt}\right) = \dot{F} * Q_P \quad \text{Equation 15}$$

The transmembrane pressure may be determined using equation 16 below, where DTMIN represents the minimum update period.

$$\text{Transmembrane pressure}(P_{TM(current)}) = P_{TM(Previous)} + \dot{F} * Q_P * DT_{MIN} \quad \text{Equation 16:}$$

The pressure of the system may be determined using equation 17 below, where $P_{INIT}$ represents initial baseline pressure.

$$\text{Pressure of the System}(P) = P_{INIT} + P_{TM} \quad \text{Equation 17:}$$

The plasma volume collected may be determined using equation 18 below. Alternatively, the plasma volume collected may be determined by weighing the plasma collected using a weight scale, for example.

$$\text{Plasma Volume Collected}(V_{P(Current)}) = V_{P(Previous)} + Q_P * DT_{MIN} \quad \text{Equation 18:}$$

The blood volume in the reservoir may be calculated using equation 19 below.

$$V_{R(Current)} = V_{R(Previous)} + Q_O * DT_{MIN} \quad \text{Equation 19:}$$

The plasma remaining to be collected may be determined using equation 20, below, and procedure time remaining and the collection time remaining may be determined using equations 11 and 12 above.

$$\text{Plasma Remaining to be Collected}(V_{PR}) = V_{PT} - V_{P(Current)} \quad \text{Equation 20:}$$

During the period of time, some or all of the above values may be iteratively determined.

After the period of time has expired, the method 900 moves to block 910 and the method 900 determines the system pressure increase with time (the slope of the acceptable fouling rate limit). In some examples, the system pressure increase with time may be determined using equation 21 below.

$$\text{Pressure Increase with Time} = \frac{(P_{Max} - P)}{\text{Collection time Remaining}} \quad \text{Equation 21}$$

At block 912, the method 900 may impose the determined pressure increase with time, determined using equation 21, for the remainder of a draw cycle. The ramp pressure may be determined using equation 22 below, where $$\frac{dP}{dt}$$

represents the pressure increase with time. Alternatively, the pressure ramp may be measured.

$$P_{TM(Current)} = P_{TM(Previous)} + \frac{dP}{dt} * DT_{MIN} \quad \text{Equation 22}$$

In some examples, a Runge-Kutta routine may be used for calculating the plasma flow rate. Equations 23-27, below, may be used in the Runge-Kutta routine, where $$FDQPDT\left(Q_P, P_{TM}, \frac{dP}{dt}, FR\right) = \frac{\left(\frac{dP}{dt} * Q_P - FR * Q_P^2\right)}{P_{TM}}.$$

$$K1 = DT_{MIN} * FDQPDT\left(Q_P, P_{TM}, \frac{dP}{dt}, FR\right) \quad \text{Equation 23}$$

$$K2 = DT_{MIN} * FDQPDT\left(Q_P + K1/2, P_{TM}, \frac{dP}{dt}, FR\right) \quad \text{Equation 24}$$

$$K3 = DT_{MIN} * FDQPDT\left(Q_P + K2/2, P_{TM}, \frac{dP}{dt}, FR\right) \quad \text{Equation 25}$$

$$K4 = DTMIN * FDQPDT\left(Q_P + K3, P_{TM}, \frac{dP}{dt}, FR\right) \quad \text{Equation 26}$$

$$Q_{P(Current)} = Q_{P(Previous)} + \frac{((K1 + 2)(K2 + 2)(K3 + K4))}{6} \quad \text{Equation 27}$$

During the remainder of the draw cycle, the method 900 may also determine the outlet flow rate ($Q_O$), outlet hematocrit ($H_O$), the volume of plasma collected ($V_P$), the volume of fluid in the reservoir ($V_R$), the fouling rate (FR), the volume of plasma remaining to be collected (VPREMAIN), the procedure time remaining (TPREMAIN) and/or the collection time remaining (TCOLREMAIN).

The outlet hematocrit may be determined using equation 28 below.

$$H_O = H_I * \frac{Q_I}{Q_O}$$ Equation 28

At block 914, the method 900 determines if the fluid volume (e.g., concentrate) in the reservoir exceeds and/or is equal to the maximum volume. If the maximum volume is not exceeded, control returns to block 914. However, if the maximum volume is exceeded, control moves to block 916, and the reservoir is drained. The reservoir may be drained at a rate represented by equation 29 below, where $Q_R$ represents the return blood flow rate.

$$V_{R(Current)} = V_{R(Previous)} - Q_R * DT_{MIN}$$ Equation 29:

At block 918, the method 900 determines whether or not the plasma volume collected is equal to the target amount. If the plasma target has not been achieved, control moves to block 910. If the plasma target has been achieved, control moves to block 920 and the method 900 determines whether or not to return to block 902. Otherwise, the example method 900 is ended.

Figure 10:
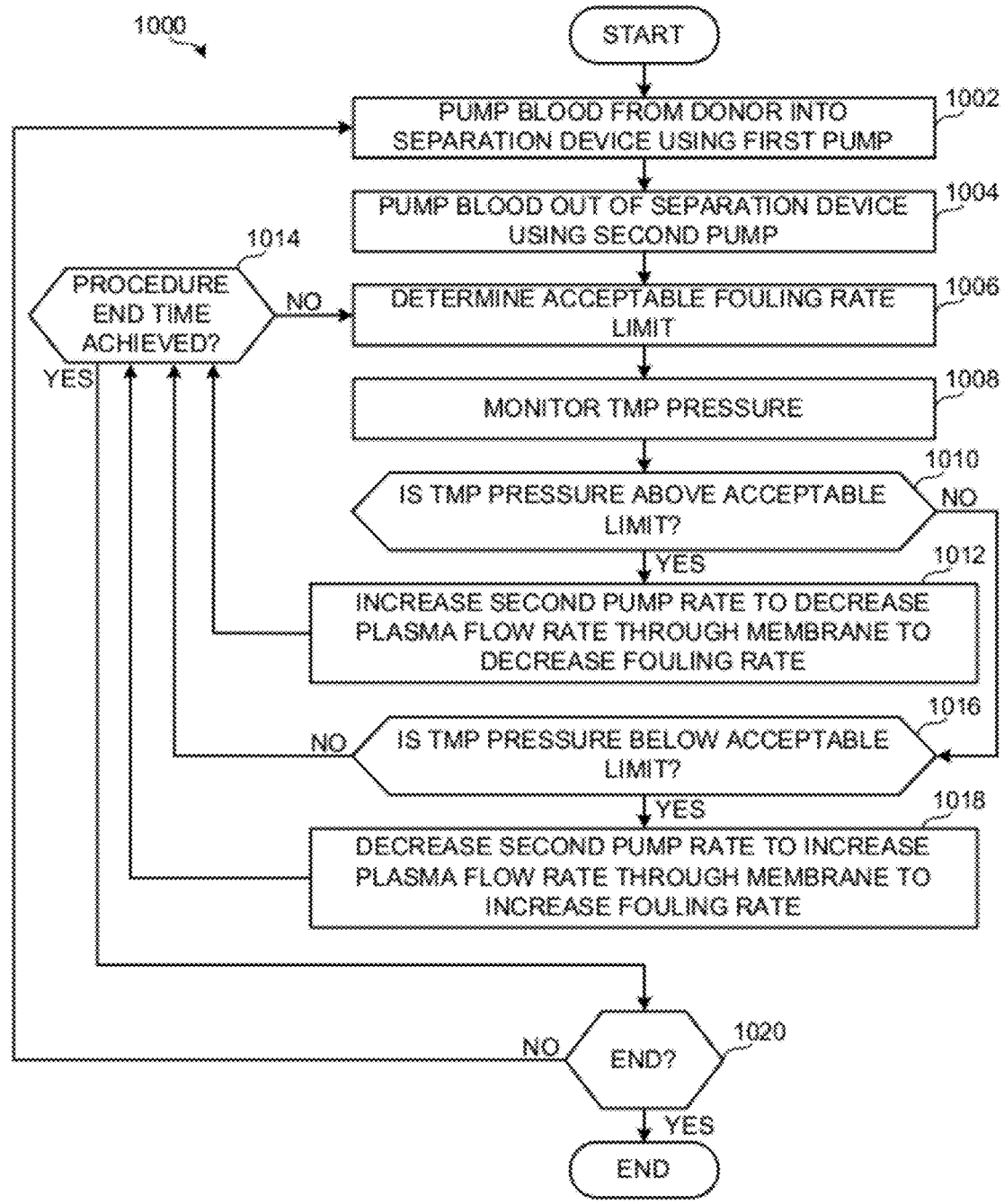

FIG. 10 relates to an example method 1000 of controlling fouling to optimize filtrate flow rate during a membrane filtration process. At block 1002, the method 1000 pumps blood (e.g., bulk fluid) from a donor into a separation device using a first pump and, at block 1004, the method 1000 pumps the blood out of the separation device using a second pump. In some examples, the blood may be pumped into the separation device at a rate of approximately 100 mL/min and the blood may be pumped out of the separation device at a rate of approximately 70 mL/min. Such a rate difference between the pumps may generate a TMP pressure that overcomes resistance of the membrane enabling plasma and/or other small blood components to flow therethrough at a rate of approximately 30 mL/min, for example.

At block 1006, the method 1000 determines an acceptable fouling rate limit. In some examples, the acceptable fouling rate limit is determined by extrapolating a line between the time and pressure at which a selected plasma flow rate (e.g., 30 mL/min) is achieved and/or a current time/pressure point and a control point. The control point may be associated with a system max and/or end time pressure and an initial estimated procedure end time and/or an updated estimated procedure end time. In some examples, the acceptable fouling rate limit may change during a plasmapheresis procedure. For example, if more membrane fouling is encountered than expected, the initial estimated procedure end time may be a lesser value than an updated estimated procedure end time determined 5 minutes into the plasmapheresis procedure. Alternatively, if less membrane fouling is encountered than expected, the initial estimated procedure end time may be a greater value than an updated estimated procedure end time determined 5 minutes into the plasmapheresis procedure.

At block 1008, the method 1000 monitors the TMP pressure. In some examples, the TMP pressure may be monitored by measuring a pressure of the bulk fluid and determining the TMP pressure therefrom. In other examples, the TMP pressure may be monitored by measuring a pressure of the bulk fluid and a pressure of the filtrate and determining the TMP pressure therefrom.

At block 1010, the method 1000 determines if the TMP pressure is above the acceptable limit and/or if the steady increase of the TMP pressure (e.g., fouling) is above the acceptable limit. In some examples, the steady increase of the TMP pressure may be above the acceptable limit if a slope of the determined TMP pressures is greater than a slope of the acceptable fouling rate limit. If the method 1000 determines that the TMP pressure is above the acceptable limit, control moves to block 1012 and the method 1000 increases the second pump rate to decrease the plasma flow rate through the membrane, thereby decreasing the fouling rate. At block 1014, the method 1000 determines if the procedure end time has been achieved. The procedure end time may be associated with the control point and/or a plasma collection target being achieved and may be iteratively determined throughout the plasmapheresis procedure. If the procedure end time has not been achieved, control moves to block 1006 and an updated acceptable fouling rate limit is determined based on the current time/pressure point (e.g., TMP pressure) and the control point.

If the method 1000 determines that the TMP pressure is not above the acceptable limit, control moves to block 1016 and the method 1000 determines if the TMP pressure is below the acceptable limit and/or if the steady increase in the TMP pressure (e.g., fouling) is below the acceptable limit. In some examples, the steady increase of the TMP pressures may be below the acceptable limit if a slope of the determined TMP pressures is less than a slope of acceptable fouling rate limit. If the method 1000 determines that the TMP pressure is below the acceptable limit, control moves to block 1018 and the method 1000 decreases the second pump rate to increase the plasma flow rate through the membrane, thereby increasing the fouling rate. At block 1014, the method 1000 determines if the procedure end time has been achieved.

If the method 1000 determines that the procedure end time has been achieved, control moves to block 1020. At block 1020, the method 1000 determines whether or not to return to block 1002. Otherwise the example method 1000 is ended.

Figure 11:
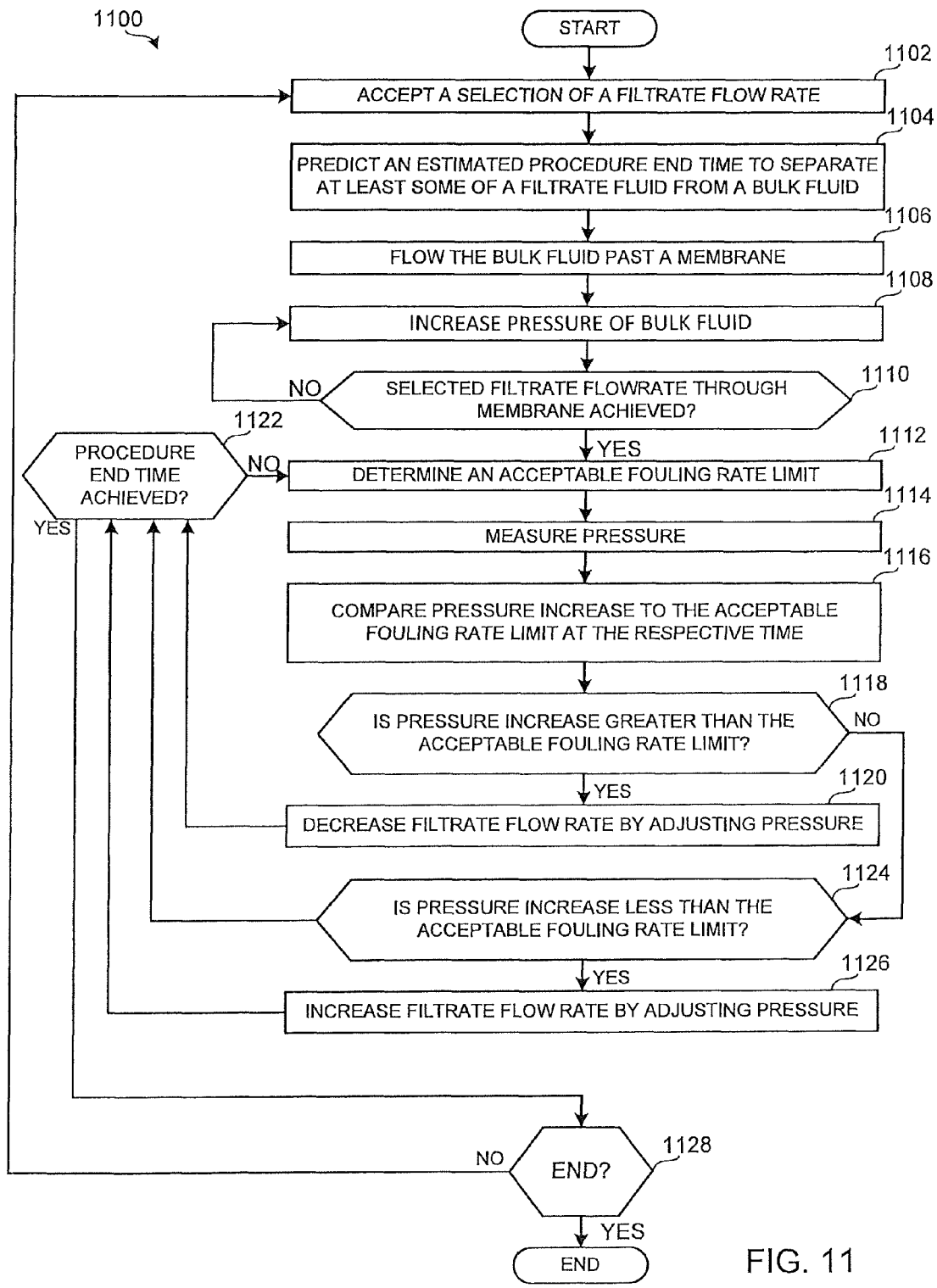

FIG. 11 relates to an example method 1100 of controlling fouling to optimize filtrate flow rate during a membrane filtration process. At block 1102, the method 1100 accepts a selection of a filtrate flow rate. In some examples, the method 1100 may receive, via an access device and/or input, a filtrate flow rate selection of approximately 30 mL/min. At block 1104, the method 1100 may predict an estimated procedure end time to separate at least some of a filtrate fluid from a bulk fluid. In some examples, the bulk fluid may be blood. In some examples, the filtrate fluid may be plasma, water, waste, etc. Regardless of the type of bulk and/or filtrate associated with the example method 1100, the estimated procedure end time may be associated with a collection target, a filtrate flow rate and, more generally, the equations described above.

At block 1106, the method 1100 flows bulk fluid past a membrane. The fluid may be pumped past a membrane using a first pump and a second pump. At block 1108, the method 1100 increases the pressure of the bulk fluid. In some examples, the pressure may be increased by having a difference between a pump rate of the first pump and a pump rate of the second pump. At block 1110, the method 1100 determines if the selected filtrate flow rate through the membrane has been achieved. In some examples, a weight scale may be used to identify when the selected filtrate flow rate has been achieved.

At block 1112, the method 1100 determines an acceptable fouling rate limit. In some examples, the acceptable fouling rate limit is determined by extrapolating a line between the time and pressure at which a selected filtrate flow rate (e.g., 30 mL/min) is achieved and/or a current time/pressure point and a control point. The control point may be associated with a system max and/or end time pressure and an initial estimated procedure end time and/or an updated procedure end time.

At block 1114, the method 1100 measures the pressure of, for example, the bulk fluid to determine the TMP pressure and/or a steady increase of the TMP pressure. At block 1116, the method 1100 compares the steady increase of the TMP pressure to the acceptable fouling rate limit. At block 1118 the method 1100 determines whether or not a slope of the measured pressures is greater than a slope of the acceptable fouling rate limit. If the method 1100 determines that the steady increase of the TMP pressure is greater than the acceptable fouling rate limit, control moves to block 1120 and the method 1100 decreases the filtrate flow rate through the membrane by dynamically adjusting the pressure. In some examples, the pressure may be adjusted by increasing the rate of the second pump such that at the next pressure measurement (e.g., the next respective time), the steady increase of the TMP pressure is similar to the acceptable fouling rate limit. In some examples, the pressure may be adjusted based on plotting the measured pressures at respective times and comparing these plotted points to the acceptable fouling rate limit to identify a difference in the slope of measured pressures at the respective times and the slope of the acceptable fouling rate limit for the respective times. If a difference (e.g., a significant difference) is identified between the two slopes, the pressure may be adjusted accordingly.

At block 1122, the method 1100 determines whether or not the procedure end time has been achieved. The procedure end time may be associated with the control point and/or a filtrate (e.g., plasma) collection target being achieved and may be iteratively determined throughout the filtration procedure. If the procedure end time has not been achieved, control moves to block 1112 and an updated acceptable fouling rate limit is determined based on the current time/pressure point (e.g., TMP pressure and the control point).

If the method 1100 determines that the steady increase of the TMP pressure is not greater than the acceptable fouling rate limit, control moves to block 1124 and the method 1100 determines whether or not the steady increase of the TMP pressure is less than the acceptable fouling rate limit. If the method 1100 determines that the steady increase of the TMP pressure is less than the acceptable fouling rate limit, control moves to block 1126 and the method 1100 increases the filtrate flow rate by dynamically adjusting the pressure. In some examples, the pressure may be adjusted by decreasing the rate of the second pump. At block 1122, the method 1100 determines if the procedure end time has been achieved.

If the method 1100 determines that the procedure end time has been achieved, control moves to block 1128. At block 1128, the method 1100 determines whether or not to return to block 1102. Otherwise the example method 1100 is ended.

Figure 12:
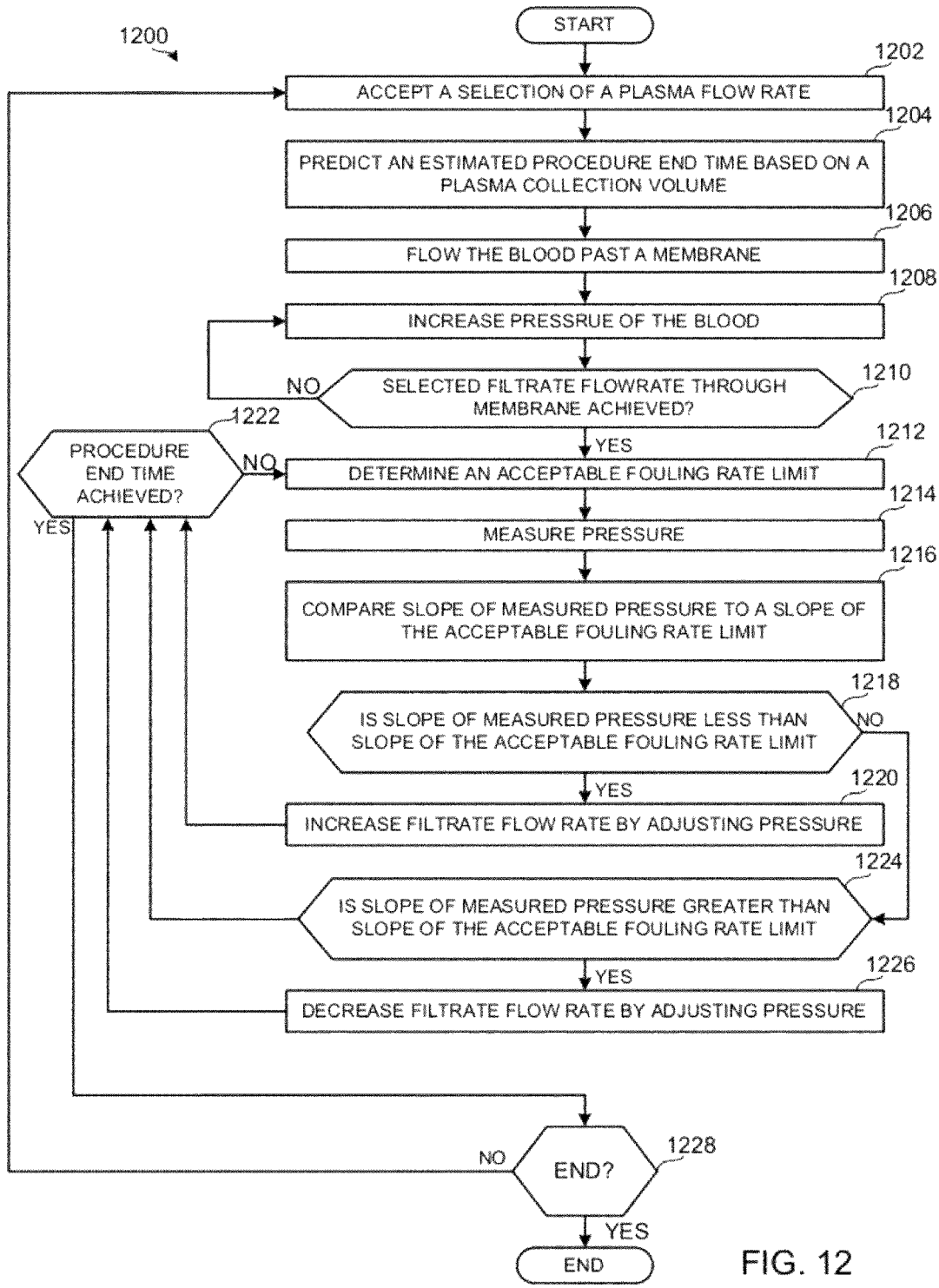

FIG. 12 relates to an example method 1200 of controlling fouling to optimize filtrate flow rate during a plasmapheresis procedure. At block 1202, the method 1200 accepts a selection of a plasma flow rate. In some examples, the method 1200 receives, via an access device and/or input, a plasma flow rate selection of approximately 30 mL/min. At block 1204, the method 1200 may predict an estimated procedure end time based on a plasma collection volume. In some examples, the estimated procedure end time may be determined using the equations described above.

At block 1206, the method 1200 flows blood past a membrane. The blood may be pumped past a membrane using a first pump and a second pump. At block 1208, the method 1200 increases the pressure of the blood. In some examples, the pressure may be increased by having a difference between the pump rate of the first pump and a pump rate of the second pump. At block 1210, the method 1200 determines if the selected filtrate flow rate through the membrane has been achieved. In some examples, a weight scale may be used to identify when the selected filtrate flow rate has been achieved.

At block 1212, the method 1200 determines an acceptable fouling rate limit. In some examples, the acceptable fouling rate limit is determined by extrapolating a line between the time and pressure at which a selected plasma flow rate (e.g., 30 mL/min) is achieved and/or a current time/pressure point and a control point. The control point may be associated with a system max and/or end time pressure and an initial estimated procedure end time and/or an updated procedure end time.

At block 1214, the method 1200 measures the pressure of, for example, the bulk fluid to determine the TMP pressure and/or a steady increase of the TMP pressure. At block 1216, the method 1200 compares the slope of the measured pressure(s) and/or the steady increase in the measured pressures to a slope of the acceptable fouling rate limit. At block 1218, the method 1200 determines if the slope of the measured pressure(s) is less than the slope of the acceptable fouling rate limit. In some examples, a slope of the measured pressure(s) being less than the slope of the acceptable fouling rate limit indicates the acceptable fouling rate limit is not being achieved and/or plasma may be demanded at a higher rate without exceeding the fouling rate limit. If the method 1200 determines that the slope of the measured pressure(s) is less than the slope of the acceptable fouling rate limit, control moves to block 1220 and the method 1200 increases the filtrate flow rate by adjusting the pressure. In some examples, the pressure may be adjusted by decreasing the rate of the second pump. At block 1222, the method 1200 determines whether or not the procedure end time has been achieved. The procedure end time may be associated with the control point and/or a plasma collection target being achieved and may be iteratively determined throughout the plasmapheresis procedure. If the procedure end time has not been achieved, control moves to block 1212 and an updated acceptable fouling rate limit may be determined based on the current time/pressure point (e.g., TMP pressure) and the control point.

If the method 1200 determines that the slope of the measured pressure(s) is not less than the slope of the acceptable fouling rate limit, control moves to block 1224. At block 1224, the method 1200 determines if the slope of the measured pressure(s) is greater than the slope of the acceptable fouling rate limit. In some examples, a slope of the measured pressure(s) being greater than the acceptable fouling rate limit indicates that the acceptable fouling rate limit is being exceeded. If the method 1200 determines that the slope of the measured pressure(s) is greater than the slope of the acceptable fouling rate limit, control moves to block 1226 and the method 1200 decreases the filtrate flow rate by adjusting the pressure. In some examples, the pressure may be adjusted by increasing the rate of the second pump. At block 1222, the method 1200 determines if the procedure end time has been achieved.

If the method 1200 determines that the procedure end time has been achieved, control moves to block 1228. At block 1228, the method 1200 determines whether or not to return to block 1202. Otherwise the example method 1200 is ended.

Figure 13:
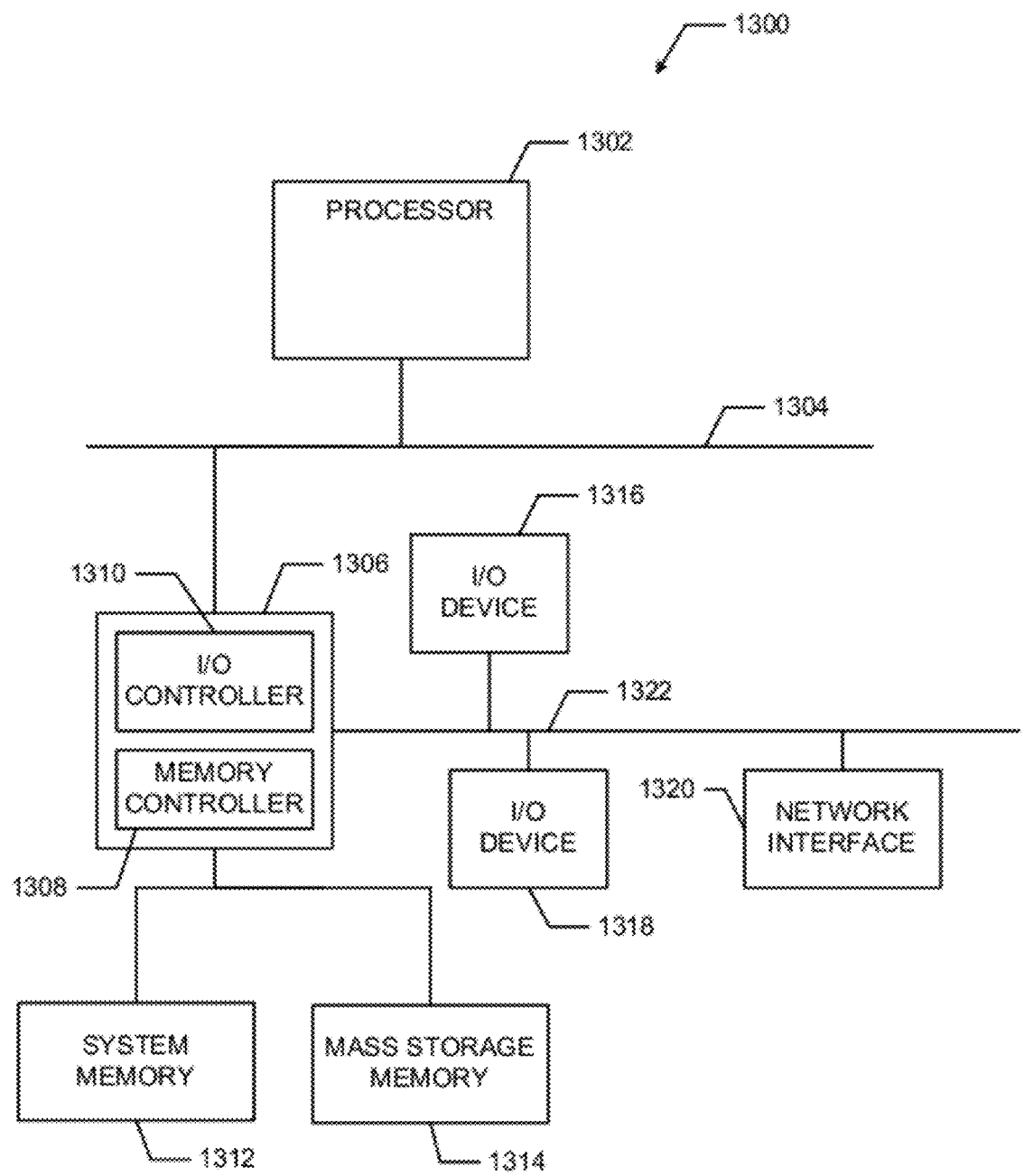
FIG. 13 is a schematic illustration of an example processor platform that may be used and/or programmed to implement any or all of the example methods and systems described herein.

FIG. 13 is a block diagram of an example processor system 1300 that may be used to pump, implement, control and/or drive the systems and methods described herein. As shown in FIG. 13, the processor system 1300 includes a processor 1302 that is coupled to an interconnection bus 1304. The processor 1302 may be any suitable processor, processing unit or microprocessor. Although not shown in FIG. 13, the processor system 1300 may be a multi-processor system and, thus, may include one or more additional processors that are identical or similar to the processor 1302 and that are communicatively coupled to the interconnection bus 1304.

The processor 1302 of FIG. 13 is coupled to a chipset 1306, which includes a memory controller 1308 and an input/output (I/O) controller 1310. As is well known, a chipset typically provides I/O and memory management functions as well as a plurality of general purpose and/or special purpose registers, timers, etc. that are accessible or used by one or more processors coupled to the chipset 1306. The memory controller 1308 performs functions that enable the processor 1302 (or processors if there are multiple processors) to access a system memory 1312 and a mass storage memory 1314.

The system memory 1312 may include any desired type of volatile and/or non-volatile memory such as, for example, static random access memory (SRAM), dynamic random access memory (DRAM), flash memory, read-only memory (ROM), etc. The mass storage memory 1314 may include any desired type of mass storage device including hard disk drives, optical drives, tape storage devices, etc.

The I/O controller 1310 performs functions that enable the processor 1302 to communicate with peripheral input/output (I/O) devices 1316 and 1318 and a network interface 1320 via an I/O bus 1322. The I/O devices 1316 and 1318 may be any desired type of I/O device such as, for example, a keyboard, a video display or monitor, a mouse, etc. The network interface 1320 may be, for example, an Ethernet device, an asynchronous transfer mode (ATM) device, an 802.11 device, a DSL modem, a cable modem, a cellular modem, etc. that enables the processor system 1300 to communicate with another processor system.

While the memory controller 1308 and the I/O controller 1310 are depicted in FIG. 13 as separate blocks within the chipset 1306, the functions performed by these blocks may be integrated within a single semiconductor circuit or may be implemented using two or more separate integrated circuits.

During a plasmapheresis procedure, blood (e.g., feed fluid, bulk fluid) drawn from a patient is pumped toward a membrane. As the blood encounters the membrane, plasma (e.g., filtrate fluid) and relatively small components of the blood may pass through the membrane while other relatively large cellular components (e.g., concentrate fluid) may not pass through the membrane. The filtrate fluid that passes through the membrane may be collected and the concentrate fluid may be returned to the donor and/or a feed reservoir. The pressure that drives the plasma flow across the membrane may be referred to as transmembrane pressure (TMP).

As the TMP pressure increases, the plasma flow rate through the membrane also increases until a concentration polarization limit (upper plasma flow rate limit) is reached. The concentration polarization limit relates to an exit hematocrit at which spinning of the membrane no longer creates proficient, adequate and/or efficient mixing for blood separation. It has been observed that a maximum plasma separation limit may coincide with an exit hematocrit of approximately 70%.

As plasma flows through the membrane, fouling and/or membrane resistance may occur that effectively clogs pores of the membrane increasing the pressure required to drive plasma through the membrane at a constant flow rate. The rate at which the membrane fouls may increase exponentially as higher plasma flow rates are demanded.

The examples described herein may use an example fouling rate control method that effectively compensates for membrane fouling and/or implements control schemas to minimize procedure times. The fouling rate may be defined as $dP_1/dt$, $dP/dt$. In contrast to some known approaches that target operating pressures and adjust plasma flow rates to achieve such operating pressures, the examples described herein target plasma flow rates and adjust the pressure to achieve such flow rates. Plasma flow rates may be associated with the blood-to-cell pump difference (e.g., the difference between a feed pump and a concentrate pump) and may not require baseline pressure measurements and/or calibration readings. Such baseline pressure measurements and/or calibration readings may reduce the efficiency and/or productivity of some known methods. Thus, using the examples described herein, the steady decrease in plasma flow rates due to membrane fouling at constant pressures may be compensated for while maximizing system efficiency.

By targeting plasma flow rates, the examples described herein may react to adverse pressure changes within the system during a plasmapheresis procedure instead of regulating the procedure based on a predicted value(s) (e.g., offset TMP pressure) used in some known methods. The predicted value may not be the most efficient value to operate the system at resulting in longer procedure times than may be possible using the examples described herein.

The example fouling rate control method may enable an example system to operate at a maximum sustainable plasma flow rate while taking membrane fouling into account as a limiting factor. The example system may use two-pumps (e.g., peristaltic pumps) and a pressure sensor to predict, control and/or maintain optimum filtrate flow rates over the life of the membrane. However, if the filtrate line is not open to atmospheric pressure, an additional pressure sensor may be positioned on the filtrate line to accurately determine TMP pressure.

In some examples, the example fouling rate control method may calculate a control point that may be used to limit the fouling rate of the membrane. The control point may be associated with a maximum and/or end time system pressure and an estimated procedure end time to achieve a plasma collection target. The control point may be recalculated throughout the procedure. During the example plasmapheresis procedure, the TMP pressure may be increased such that once the plasma collection target is reached, the maximum and/or end time system pressure may be simultaneously reached, thereby maximizing the efficiency of the plasmapheresis procedure.

In some examples, an acceptable fouling rate limit is determined by extrapolating a line between a measured control pressure at an elapsed procedure time when a selected plasma flow rate is achieved and/or a current measured pressure (e.g., a first point) and the control point (e.g., a second point). The acceptable fouling rate limit may be recalculated throughout the procedure. Using this extrapolation, an acceptable fouling rate may be determined at all times during the plasmapheresis procedure and, thus, the fouling rate of the membrane may be controlled during the entire procedure. For example, based on the extrapolation, during the plasmapheresis procedure, the system may increase the TMP pressure by 5 mmHg every minute to achieve the desired plasma flow rate without causing the membrane to foul. In some examples, the plasma flow rate and/or the amount of collected plasma may be determined using a weight scale.

During the plasmapheresis procedure, if the slope between the current TMP (e.g., current measured TMP) at an elapsed procedure time and the control point is different than the slope of at least some of the measured TMPs, including the current TMP, the plasma flow rate demanded may be adjusted accordingly. For example, if the slope between the current TMP at an elapsed procedure time and the control point is greater than the slope of at least some of the measured TMPs, including the current TMP (e.g., the rate of increase of the TMP pressure is too low), the plasma flow rate demanded may be increased to enable a slope of the next measured pressures to be similar and/or match a slope between the next TMP and the control point (e.g., the new fouling rate limit). Thus, the fouling rate limit may be dynamically adjusted during a filtration procedure based on the current TMP and/or an updated estimated end time. Alternatively, for example, if the slope between the current TMP at an elapsed procedure time and the control point is less than the slope of at least some of the measured TMPs, including the current TMP (e.g., the rate of increase of the TMP pressure is too high), the plasma flow rate demanded may be decreased to enable a slope of the next measured pressures to be similar and/or match a slope between the next TMP and the control point (e.g., the new fouling rate limit). Because the calculation of an instantaneous fouling rate may not be possible, the example systems and methods may average and/or predict a future fouling rate(s) based on the measured control pressure and the procedure time elapsed, for example.

In some examples, during the plasmapheresis procedure, the TMP pressure may change during pre-identified intervals. These pre-identified intervals may include cycle transitions, plasma line priming, etc. During such pre-identified intervals, the plasma flow control may be temporarily disabled until the TMP pressure is reachieved and/or when control is reachieved, for example.

Although certain example methods, apparatus and articles of manufacture have been described herein, the scope of coverage of this patent is not limited thereto. On the contrary, this patent covers all methods, apparatus and articles of manufacture fairly falling within the scope of the appended claims either literally or under the doctrine of equivalents.

What is claimed:

1. A method of controlling fouling of a membrane during a fluid filtering process, comprising:
    accepting a selected filtrate flow rate;
    selecting a maximum transmembrane pressure;
    predicting an estimated procedure end time to separate at least a portion of a filtrate fluid from a bulk fluid;
    calculating a control point corresponding to the maximum transmembrane pressure and the estimated procedure end time;
    flowing the bulk fluid past the membrane;
    achieving the selected filtrate flow rate through the membrane;
    determining a transmembrane pressure and time elapsed when the selected filtrate flow rate is achieved;
    determining an acceptable fouling rate, as defined by a slope of a plot of a current transmembrane pressure and the control point, and a slope of a plot of periodically-measured transmembrane pressures versus time;
    comparing the two slopes to determine an acceptable rate of change with time of the transmembrane pressure; and
    adjusting the filtrate flow rate based on the determined acceptable rate of change with time of the transmembrane pressure to cause the plot of periodically-measured transmembrane pressures versus time to approximate the plot of the acceptable fouling rate.

2. The method of claim 1, wherein the acceptable rate of change with time of the transmembrane pressure is determined from a first point associated with the pressure and time elapsed when the selected filtrate flow rate is achieved and a second point associated with the estimated procedure end time and a system pressure at the estimated procedure end time.

3. The method of claim 2, wherein the acceptable rate of pressure change with time is determined by extrapolating between the first point and the second point.

4. The method of claim 2, wherein the acceptable rate of pressure change with time comprises a slope between the first point and the second point.

5. The method of claim 1, wherein adjusting the filtrate flow rate comprises adjusting a pressure increase rate of the bulk fluid flowing past the membrane based on a difference between a measured pressure at a respective time and the acceptable fouling rate limit for the respective time.

6. The method of claim 1, wherein the filtrate fluid comprises plasma.

7. The method of claim 1, wherein the fluid filtering process comprises a plasmapheresis process.

8. The method of claim 1, wherein the fluid filtering process comprises a dialysis process.

9. The method of claim 1, wherein adjusting the filtrate flow rate is to enable a measured pressure at a next respective time to correspond to a pressure associated with an updated rate of pressure change with time for the next respective time.

10. The method of claim 1, wherein adjusting the filtrate flow rate is to enable a slope of measured pressures to be similar to a slope between an estimated procedure end time and a system pressure at the estimated procedure end time and a measured pressure at a next measured time.

11. The method of claim 1, wherein adjusting the filtrate flow rate comprises dynamically adjusting the filtrate flow rate based on a comparison of the transmembrane pressure to the acceptable rate of change with time of the transmembrane pressure.

12. The method of claim 1, wherein the estimated procedure end time is predicated at least partially based on a filtrate collection target volume.

13. The method of claim 12, wherein the filtrate collection target volume comprises a plasma collection target volume.

14. The method of claim 1, further comprising disabling adjusting the filtrate flow rate during preidentified intervals.

15. The method of claim 14, wherein the preidentified intervals comprise at least one of a cycle time transition, or line priming.

16. The method of claim 14, further comprising reenabling adjusting the filtrate flow rate when the selected filtrate flow rate is reachieved after the preidentified interval.

17. The method of claim 1, wherein adjusting the filtrate flow rate comprises comparing measured transmembrane pressures at respective times to the acceptable rate of pressure change with time of the transmembrane pressure to identify a difference between a slope of the measured transmembrane pressures at the respective times and a slope of the acceptable rate of change with time of the transmembrane pressures for the respective times and adjusting the filtrate flow rate based on the difference.

18. The method of claim 1, wherein adjusting the filtrate flow rate comprises adjusting a pressure of the bulk fluid to enable the measured pressure at the next respective time to be similar to the pressure associated with an rate of pressure change with time for the next respective time.

19. The method of claim 1, wherein changing the filtrate flow rate until the selected filtrate flow rate through the membrane is achieved comprises increasing a pressure of the bulk fluid until the selected filtrate flow rate through the membrane is achieved.

20. A method of controlling fouling of a membrane during a fluid filtering process, comprising:
    selecting a maximum transmembrane pressure;
    predicting an estimated procedure end time to separate a collection target of a filtrate fluid from a bulk fluid;

calculating a control point corresponding to the maximum transmembrane pressure and the estimated procedure end time;

flowing the bulk fluid past the membrane;

periodically measuring a transmembrane pressure;

plotting the periodically-measured transmembrane pressures versus time and determining the slope thereof;

plotting a current transmembrane pressure versus time and the control point and determining the slope thereof, so as to define an acceptable fouling rate; and adjusting the transmembrane pressure based on a comparison of the slopes so that, as the transmembrane pressure continues to be periodically measured, the slope of the periodically-measured transmembrane pressures versus time approximates the slope of the plot defining the acceptable fouling rate.

21. The method of claim 20 wherein the control point corresponds to simultaneous achievement of the collection target and the maximum transmembrane pressure.

22. The method of claim 20 further comprising recalculating the control point at periodic intervals during the process.

23. The method of claim 20 further comprising recalculating the control point when the transmembrane pressure is periodically measured.

* * * * *